(12) United States Patent
Lee et al.

(10) Patent No.: US 12,188,824 B2
(45) Date of Patent: Jan. 7, 2025

(54) METHOD AND ELECTRONIC DEVICE FOR DETECTING WEARING USING POLARIZATION

(71) Applicant: Samsung Electronics Co., Ltd., Suwon-si (KR)

(72) Inventors: Jeahyuck Lee, Suwon-si (KR); Hyunguk Yoo, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 296 days.

(21) Appl. No.: 17/746,335

(22) Filed: May 17, 2022

(65) Prior Publication Data
US 2022/0364924 A1    Nov. 17, 2022

Related U.S. Application Data

(63) Continuation of application No. PCT/KR2022/002899, filed on Mar. 2, 2022.

(30) Foreign Application Priority Data

May 14, 2021 (KR) .................. 10-2021-0062764

(51) Int. Cl.
*G01J 4/04* (2006.01)
*A61B 5/024* (2006.01)

(52) U.S. Cl.
CPC ............ *G01J 4/04* (2013.01); *A61B 5/02427* (2013.01)

(58) Field of Classification Search
CPC .............................. G01J 4/04; A61B 5/02427
See application file for complete search history.

(56) References Cited

U.S. PATENT DOCUMENTS 6,122,042 A * 9/2000 Wunderman ........ A61B 1/0607
356/73
6,353,226 B1 * 3/2002 Khalil .................... G01N 21/49
600/323

(Continued)

FOREIGN PATENT DOCUMENTS

CN          111265200 A      6/2020
JP          10-211176 A      8/1998

(Continued)

OTHER PUBLICATIONS

International Search Report dated Jun. 2, 2022, issued in International Patent Application No. PCT/KR2022/002899.

*Primary Examiner* — Edmond C Lau
*Assistant Examiner* — Jarreas Underwood
(74) *Attorney, Agent, or Firm* — Jefferson IP Law, LLP

(57) ABSTRACT

An electronic device is provided. The electronic device includes a lighting-emitting diode (LED) module configured to emit light of a first polarization direction, a first photodiode configured to receive the light emitted from the LED module through a first polarizer having the first polarization direction, a second photodiode configured to receive the light emitted from the LED module through a second polarizer having a second polarization direction perpendicular to the first polarization direction, and a processor configured to determine wearing information of the electronic device based on luminous intensity of light sensed from each of the first photodiode and the second photodiode.

21 Claims, 13 Drawing Sheets

(56) References Cited

U.S. PATENT DOCUMENTS

| | | | | |
|---|---|---|---|---|
| 6,587,703 B2* | 7/2003 | Cheng | ............... | A61B 5/14551 |
| | | | | 600/328 |
| 7,440,659 B2* | 10/2008 | Liu | ................... | G01N 21/4738 |
| | | | | 385/39 |
| 7,460,248 B2* | 12/2008 | Kurtz | ................ | G01N 21/6458 |
| | | | | 356/497 |
| 8,373,859 B2* | 2/2013 | Chhibber | ............... | H04N 23/50 |
| | | | | 382/165 |
| 10,181,021 B2* | 1/2019 | Venkatraman | ......... | G06F 21/32 |
| 10,736,580 B2 | 8/2020 | Newberry | | |
| 2007/0263226 A1* | 11/2007 | Kurtz | ................ | G01N 21/4795 |
| | | | | 356/492 |
| 2016/0007925 A1 | 1/2016 | Mirov et al. | | |
| 2016/0341600 A1* | 11/2016 | Aloe | ....................... | G01V 8/12 |
| 2018/0279892 A1* | 10/2018 | Qi | ....................... | A61B 5/7214 |
| 2018/0338721 A1* | 11/2018 | Wang | .................. | A61B 5/0205 |
| 2019/0050622 A1 | 2/2019 | Cabibihan et al. | | |
| 2020/0345234 A1* | 11/2020 | Li | ....................... | A61B 5/0059 |
| 2020/0410079 A1 | 12/2020 | Gu | | |

FOREIGN PATENT DOCUMENTS

| | | | |
|---|---|---|---|
| JP | 2016-32631 A | | 3/2016 |
| JP | 2019045247 A | | 3/2019 |
| KR | 10-2016-0096494 A | | 8/2016 |
| KR | 10-2017-0033755 A | | 3/2017 |
| KR | 20170033755 A | * | 3/2017 |
| KR | 10-2018-0054783 A | | 5/2018 |
| KR | 10-2020-0144279 A | | 12/2020 |

* cited by examiner

METHOD AND ELECTRONIC DEVICE FOR DETECTING WEARING USING POLARIZATION

CROSS-REFERENCE TO RELATED APPLICATION(S)

This application is a continuation application, claiming priority under § 365(c), of an International application No. PCT/KR2022/002899, filed on Mar. 2, 2022, which is based on and claims the benefit of a Korean patent application number 10-2021-0062764, filed on May 14, 2021, in the Korean Intellectual Property Office, the disclosure of which is incorporated by reference herein in its entirety.

BACKGROUND

1. Field

The disclosure relates to a method and an electronic device for detecting whether the electronic device is worn using polarization and selectively measuring a biosignal.

2. Description of Related Art

A wearing detection technology determines whether an electronic device (e.g., a wearable device) is worn, and more particularly, determines whether the electronic device is worn and a wearing state of the electronic device. The waring detection technology may be required for a normal operation of the electronic device. The wearing detection technology may be classified into an optical operation and an electrical operation. The optical operation may optically detect whether the electronic device is worn by measuring heart rate, stress, or saturation of partial pressure oxygen (SpO2) in the blood using a photoplethysmogram (PPG) sensor. The PPG sensor may measure a biosignal of a user by emitting light from a light-emitting diode (LED) and receiving the light by a photodiode. When the PPG sensor uses a green LED that emits light having a wavelength range of approximately 520 nanometers (nm) to 565 nm, skin permeability may be relatively low although a stable signal is obtained even with a movement of the user. When the PPG sensor uses a red LED that emits light having a wavelength range of approximately 660 nm or an infrared ray LED that emits light having a wavelength range of approximately 880 nm to 940 nm, a signal to be measured may be weak and it may be susceptible to a movement of the user although skin permeability is relatively high.

The above information is presented as background information only to assist with an understanding of the disclosure. No determination has been made, and no assertion is made, as to whether any of the above might be applicable as prior art with regard to the disclosure.

SUMMARY

A typical wearing detection technology may not be effective for continuous and stable wearing detection because it is vulnerable to detection performed when there is an intense movement of a user and wearing is loose. Of the typical wearing detection technology, a technology for detecting wearing using the amount of light reflected from the surface of an object may detect wearing on a living object while being erroneously operating on other objects (e.g., a banana or a teddy bear) that are not a living object or erroneously operating in water. According to an embodiment, an electronic device may accurately detect whether it is worn using polarization even in a case where there is a movement of a user and where it is loosely worn, thereby being effective for continuous and stable wearing detection.

In addition, a typical method of measuring a biosignal of a user using an infrared lighting-emitting diode (LED) or a red LED may not perform a precise measurement because it is susceptible to a movement of the user and a lot of noise is generated during running or vigorous exercise. Accordingly, a green LED may be typically used to measure a biosignal of a user. However, skin permeability may be low, and thus a biosignal may not be accurately measured. When the wearing is not in a desirable state, the performance of measuring a biosignal and detecting the wearing may be further degraded. However, according to an embodiment, an electronic device may include a plurality of photodiodes configured to receive polarized light, and measure a signal using the photodiodes to which different polarizers are applied according to a wearing state of the electronic device, thereby more accurately measuring a biosignal of a user regardless of a type of an LED.

Aspects of the disclosure are to address at least the above-mentioned problems and/or disadvantages and to provide at least the advantages described below. Accordingly, an aspect of the disclosure is to provide a method and an electronic device for detecting whether the electronic device is worn using polarization and selectively measuring a biosignal.

Additional aspects will be set forth in part in the description which follows and, in part, will be apparent from the description, or may be learned by practice of the presented embodiments.

In accordance with an aspect of the disclosure, an electronic device is provided. The electronic device includes an LED configured to emit light of a first polarization direction, a first photodiode configured to receive the light emitted from the LED through a first polarizer having the first polarization direction, a second photodiode configured to receive the light emitted from the LED through a second polarizer having a second polarization direction perpendicular to the first polarization direction, and a processor configured to determine wearing information of the electronic device based on luminous intensity of light sensed from each of the first photodiode and the second photodiode.

In accordance with another aspect of the disclosure, a method performed by an electronic device is provided. The method includes emitting light of a first polarization direction, receiving, by a first photodiode, the emitted light through a first polarizer having the first polarization direction, receiving, by a second photodiode, the emitted light through a second polarizer having a second polarization direction perpendicular to the first polarization direction, and determining wearing information of the electronic device based on luminous intensity of light sensed from each of the first photodiode and the second photodiode.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
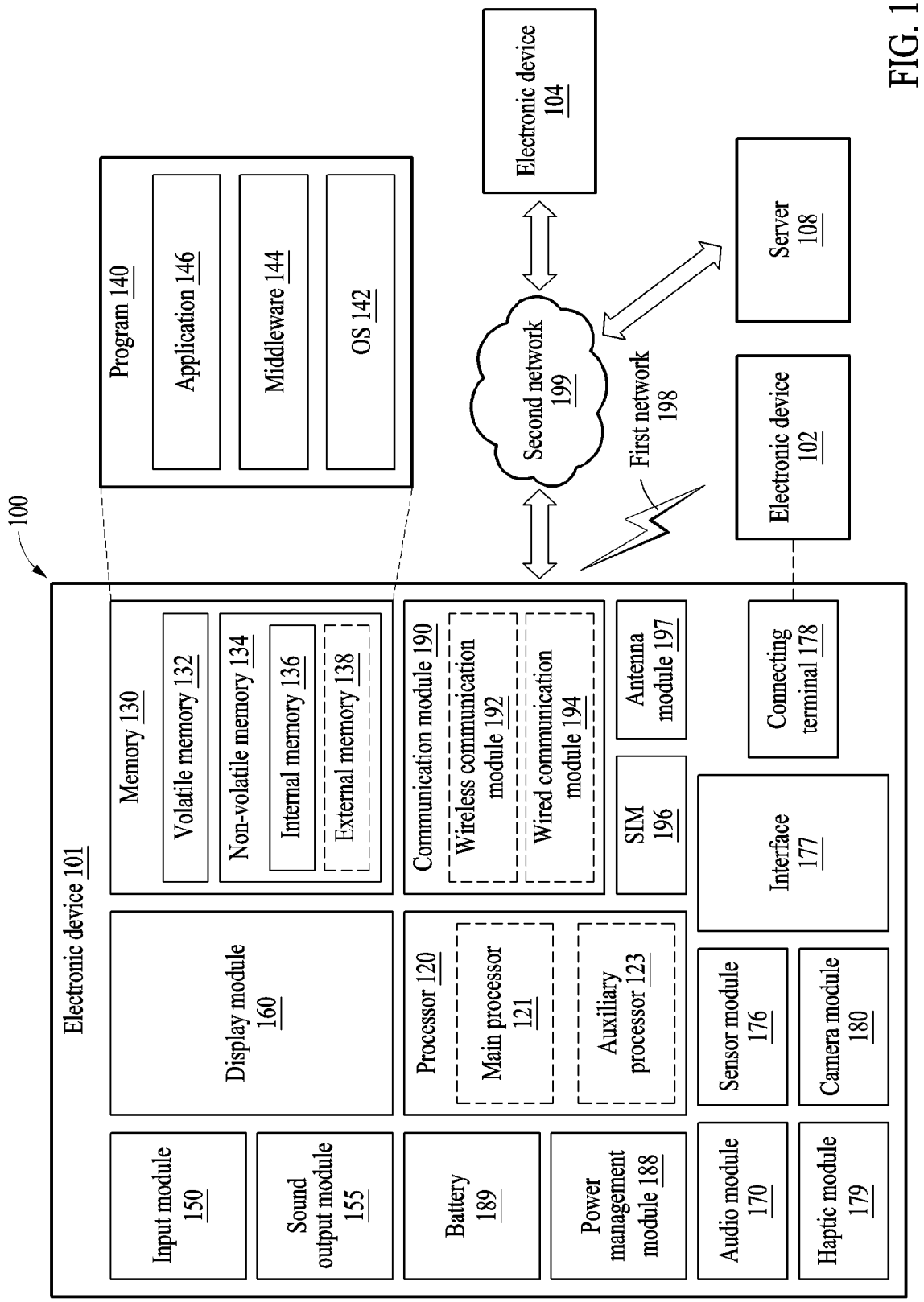
FIG. 1 is a block diagram illustrating an example electronic device in a network environment according to an embodiment of the disclosure.

FIG. 1 is a block diagram illustrating an example electronic device in a network environment according to an embodiment of the disclosure.

Figure 2A:
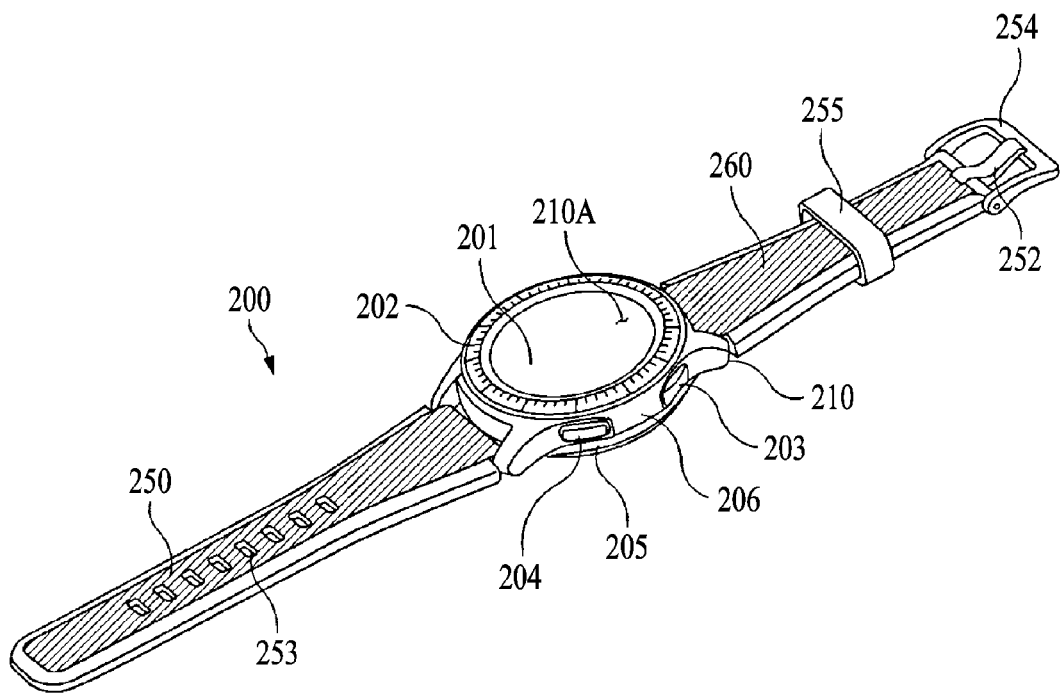
FIGS. 2A and 2B are perspective views of an electronic device according to various embodiments of the disclosure.
Figure 2B:
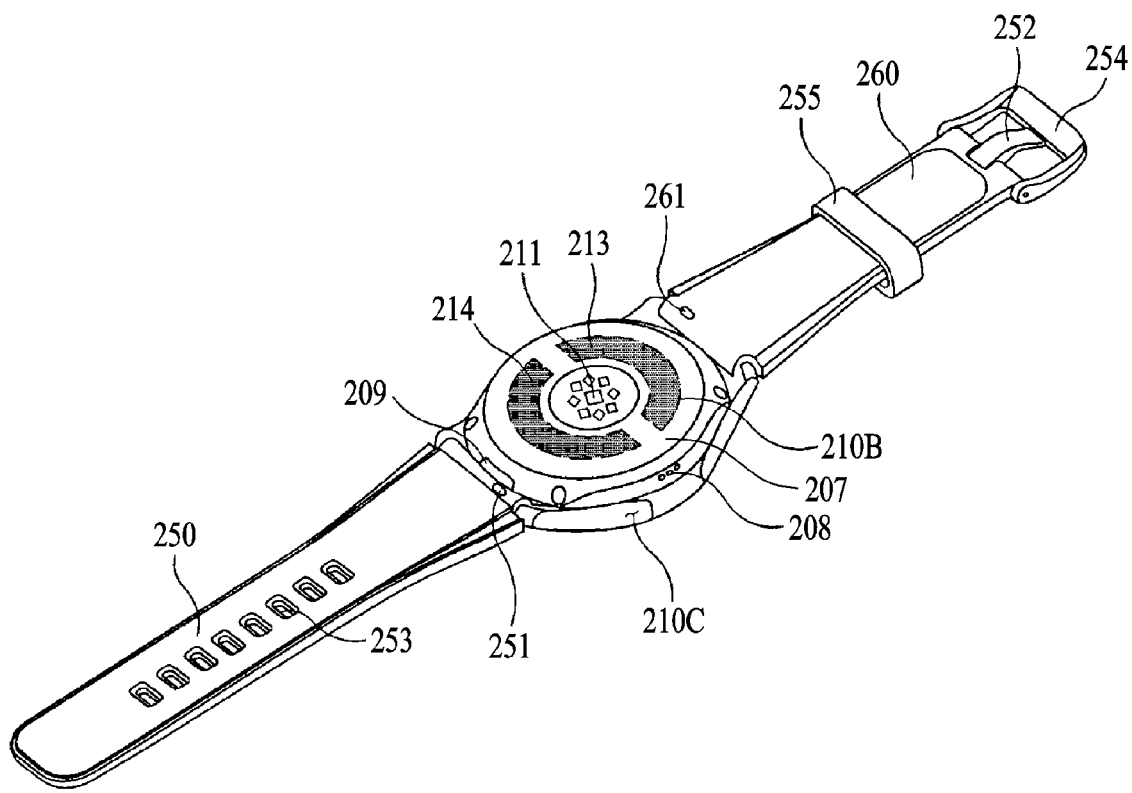

FIGS. 2A and 2B are perspective views of an electronic device according to various embodiments of the disclosure.

Figure 3:
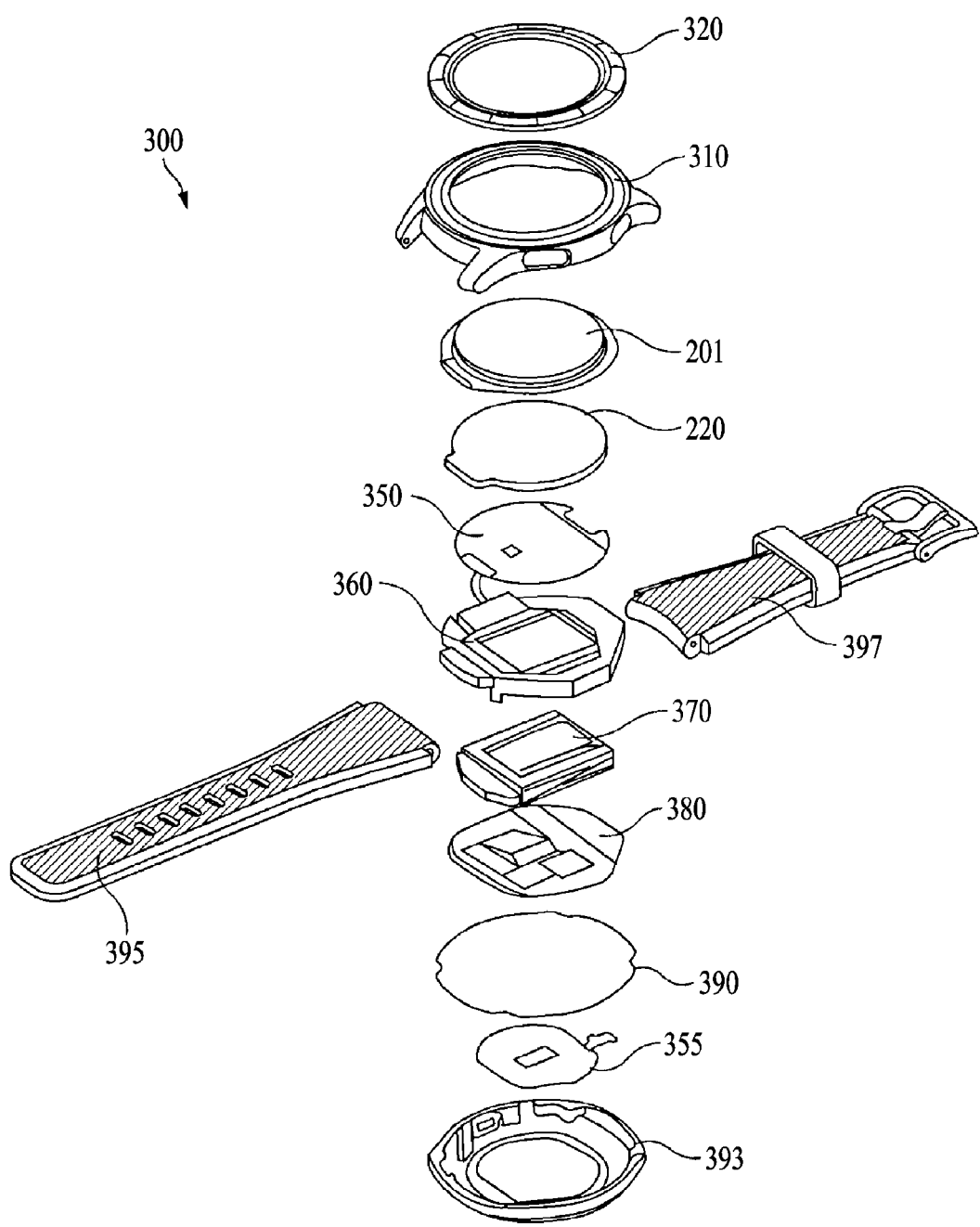
FIG. 3 is an exploded perspective view of an electronic device according to an embodiment of the disclosure.

FIG. 3 is an exploded perspective view of an electronic device according to an embodiment of the disclosure.

Referring to FIG. 1, an electronic device 101 in a network environment 100 may communicate with an electronic device 102 via a first network 198 (e.g., a short-range wireless communication network), or communicate with at least one of an electronic device 104 and a server 108 via a second network 199 (e.g., a long-range wireless communication network). According to an example embodiment, the electronic device 101 may communicate with the electronic device 104 via the server 108. According to an example embodiment, the electronic device 101 may include a processor 120, a memory 130, an input module 150, a sound output module 155, a display module 160, an audio module 170, and a sensor module 176, an interface 177, a connecting terminal 178, a haptic module 179, a camera module 180, a power management module 188, a battery 189, a communication module 190, a subscriber identification module (SIM) 196, or an antenna module 197. In some example embodiments, at least one (e.g., the connecting terminal 178) of the above components may be omitted from the electronic device 101, or one or more other components may be added in the electronic device 101. In some example embodiments, some (e.g., the sensor module 176, the camera module 180, or the antenna module 197) of the components may be integrated as a single component (e.g., the display module 160).

The processor 120 may execute, for example, software (e.g., a program 140) to control at least one other component (e.g., a hardware or software component) of the electronic device 101 connected to the processor 120, and may perform various data processing or computation. According to an example embodiment, as at least a part of data processing or computation, the processor 120 may store a command or data received from another component (e.g., the sensor module 176 or the communication module 190) in a volatile memory 132, process the command or data stored in the volatile memory 132, and store resulting data in a non-volatile memory 134. According to an example embodiment, the processor 120 may include a main processor 121 (e.g., a central processing unit (CPU) or an application processor (AP)) or an auxiliary processor 123 (e.g., a graphics processing unit (GPU), a neural processing unit (NPU), an image signal processor (ISP), a sensor hub processor, or a communication processor (CP)) that is operable independently of, or in conjunction with, the main processor 121. For example, when the electronic device 101 includes the main processor 121 and the auxiliary processor 123, the auxiliary processor 123 may be adapted to consume less power than the main processor 121 or to be specific to a specified function. The auxiliary processor 123 may be implemented separately from the main processor 121 or as a part of the main processor 121.

The auxiliary processor 123 may control at least some of functions or states related to at least one (e.g., the display module 160, the sensor module 176, or the communication module 190) of the components of the electronic device 101, instead of the main processor 121 while the main processor 121 is in an inactive (e.g., sleep) state or along with the main processor 121 while the main processor 121 is an active state (e.g., executing an application). According to an example embodiment, the auxiliary processor 123 (e.g., an ISP or a CP) may be implemented as a portion of another component (e.g., the camera module 180 or the communication module 190) that is functionally related to the auxiliary processor 123. According to an example embodiment, the auxiliary processor 123 (e.g., an NPU) may include a hardware structure specified for artificial intelligence (AI) model processing. An AI model may be generated by machine learning. Such learning may be performed by, for example, the electronic device 101 in which the AI model is performed, or performed via a separate server (e.g., the server 108). Learning algorithms may include, but are not limited to, for example, supervised learning, unsupervised learning, semi-supervised learning, or reinforcement learning. The AI model may include a plurality of artificial neural network layers. An artificial neural network may include, for example, a deep neural network (DNN), a convolutional neural network (CNN), a recurrent neural network (RNN), a restricted Boltzmann machine (RBM), a deep belief network (DBN), and a bidirectional recurrent deep neural network (BRDNN), a deep Q-network, or a combination of two or more thereof, but is not limited thereto. The AI model may alternatively or additionally include a software structure other than the hardware structure.

The memory 130 may store various data used by at least one component (e.g., the processor 120 or the sensor module 176) of the electronic device 101. The data may include, for example, software (e.g., the program 140) and input data or output data for a command related thereto. The memory 130 may include the volatile memory 132 or the non-volatile memory 134. The non-volatile memory 134 may include an internal memory 136 and an external memory 138.

The program 140 may be stored as software in the memory 130, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output a sound signal to the outside of the electronic device 101. The sound output module 155 may include, for example, a speaker or a receiver. The speaker may be used for general purposes, such as playing multimedia or playing records. The receiver may be used to receive an incoming call. According to an example embodiment, the receiver may be implemented separately from the speaker or as a part of the speaker.

The display module 160 may visually provide information to the outside (e.g., a user) of the electronic device 101. The display module 160 may include, for example, a display, a hologram device, or a projector, and a control circuitry to control a corresponding one of the display, the hologram device, and the projector. According to an example embodiment, the display module 160 may include a touch sensor adapted to sense a touch, or a pressure sensor adapted to measure an intensity of a force incurred by the touch.

The audio module 170 may convert a sound into an electric signal or vice versa. According to an example embodiment, the audio module 170 may obtain the sound via the input module 150 or output the sound via the sound output module 155 or an external electronic device (e.g., the electronic device 102 such as a speaker or a headphone) directly or wirelessly connected to the electronic device 101.

The sensor module 176 may detect an operational state (e.g., power or temperature) of the electronic device 101 or an environmental state (e.g., a state of a user) external to the electronic device 101, and generate an electric signal or data value corresponding to the detected state. According to an example embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with an external electronic device (e.g., the electronic device 102) directly (e.g., wiredly) or wirelessly. According to an example embodiment, the interface 177 may include, for example, a high-definition multimedia interface (HDMI), a universal serial bus (USB) interface, a secure digital (SD) card interface, or an audio interface.

The connecting terminal 178 may include a connector via which the electronic device 101 may be physically connected to an external electronic device (e.g., the electronic device 102). According to an example embodiment, the connecting terminal 178 may include, for example, an HDMI connector, a USB connector, an SD card connector, or an audio connector (e.g., a headphone connector).

The haptic module 179 may convert an electric signal into a mechanical stimulus (e.g., a vibration or a movement) or an electrical stimulus which may be recognized by a user via his or her tactile sensation or kinesthetic sensation. According to an example embodiment, the haptic module 179 may include, for example, a motor, a piezoelectric element, or an electric stimulator.

The camera module 180 may capture a still image and moving images. According to an example embodiment, the camera module 180 may include one or more lenses, image sensors, ISPs, or flashes.

The power management module 188 may manage power supplied to the electronic device 101. According to an example embodiment, the power management module 188 may be implemented as, for example, at least a part of a power management integrated circuit (PMIC).

The battery 189 may supply power to at least one component of the electronic device 101. According to an example embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and an external electronic device (e.g., the electronic device 102, the electronic device 104, or the server 108) and performing communication via the established communication channel. The communication module 190 may include one or more communication processors that are operable independently of the processor 120 (e.g., an AP) and that support direct (e.g., wired) communication or wireless communication. According to an example embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device 104 via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5$^{th}$ generation (5G) network, a next-generation communication network, the Internet, or a computer network (e.g., a LAN or a wide area network (WAN)). These various types of communication modules may be implemented as a single component (e.g., a single chip), or may be implemented as multiple components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the SIM 196.

The wireless communication module 192 may support a 5G network after a 4$^{th}$ generation (4G) network, and a next-generation communication technology, e.g., a new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., a mmWave band) to achieve, e.g., a high data transmission rate. The wireless communication module 192 may support various technologies for securing performance on a high-frequency band, such as, e.g., beamforming, massive multiple-input and multiple-output (MIMO), full dimensional MIMO (FD-MIMO), an array antenna, analog beamforming, or a large scale antenna. The wireless communication module 192 may support various requirements specified in the electronic device 101, an external electronic device (e.g., the electronic device 104), or a network system (e.g., the second network 199). According to an example embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., an external electronic device) of the electronic device 101. According to an example embodiment, the antenna module 197 may include an antenna including a radiating element including a conductive material or a conductive pattern formed in or on a substrate (e.g., a printed circuit board (PCB)). According to an example embodiment, the antenna module 197 may include a plurality of antennas (e.g., array antennas). In such a case, at least one antenna appropriate for a communication scheme used in a communication network, such as the first network 198 or the second network 199, may be selected by, for example, the communication module 190 from the plurality of antennas. The signal or the power may be transmitted or received between the communication module 190 and the external electronic device via the at least one selected antenna. According to an example embodiment, another component (e.g., a radio frequency integrated circuit (RFIC)) other than the radiating element may be additionally formed as a part of the antenna module 197.

According to various example embodiments, the antenna module 197 may form an mmWave antenna module. According to an example embodiment, the mmWave antenna module may include a PCB, an RFIC disposed on a first surface (e.g., a bottom surface) of the PCB or adjacent to the first surface and capable of supporting a designated high-frequency band (e.g., the mmWave band), and a plurality of antennas (e.g., array antennas) disposed on a second surface (e.g., a top or a side surface) of the PCB or adjacent to the second surface and capable of transmitting or receiving signals in the designated high-frequency band.

At least some of the above-described components may be coupled mutually and communicate signals (e.g., commands or data) therebetween via an inter-peripheral communication scheme (e.g., a bus, general-purpose input and output (GPIO), serial peripheral interface (SPI), or mobile industry processor interface (MIPI)).

According to an example embodiment, commands or data may be transmitted or received between the electronic device 101 and the external electronic device 104 via the server 108 coupled with the second network 199. Each of the external electronic devices 102 and 104 may be a device of the same type as or a different type from the electronic device 101. According to an example embodiment, all or some of operations to be executed by the electronic device 101 may be executed at one or more of the external electronic devices 102 and 104, and the server 108. For example, if the electronic device 101 needs to perform a function or a service automatically, or in response to a request from a user or another device, the electronic device 101, instead of, or in addition to, executing the function or the service, may request one or more external electronic devices to perform at least a part of the function or the service. The one or more external electronic devices receiving the request may perform the at least part of the function or the service requested, or an additional function or an additional service related to the request, and may transfer an outcome of the performing to the electronic device 101. The electronic device 101 may provide the outcome, with or without further processing of the outcome, as at least a part of a reply to the request. To that end, a cloud computing, distributed computing, mobile edge computing (MEC), or client-server computing technology may be used, for example. The electronic device 101 may provide ultra-low latency services using, e.g., distributed computing or mobile edge computing. In an example embodiment, the external electronic device 104 may include an Internet-of-things (IoT) device. The server 108 may be an intelligent server using machine learning and/or a neural network. According to an example embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Referring to FIGS. 2A and 2B, according to an embodiment, an electronic device 200 (e.g., the electronic device 101 of FIG. 1) may include a housing 210 including a first surface (or a front surface) 210A, a second surface (or a back surface) 210B, and a side surface 210C surrounding a space between the first surface 210A and the second surface 210B, and fastening members 250 and 260 connected to at least a portion of the housing 210 and configured to detachably attach the electronic device 200 to a body part (e.g., a wrist, an ankle, etc.) of a user. According to another embodiment (not shown), a housing may refer to a structure that forms a portion of the first surface 210A, the second surface 210B, and the side surface 210C illustrated in FIGS. 2A and 2B. According to an embodiment, the first surface 210A may be formed by a front plate 201 (e.g., a glass plate or a polymer plate including various coating layers) of which at least a portion is substantially transparent. The second surface 210B may be formed by a back plate 207 that is substantially opaque. The back plate 207 may be formed of, for example, coated or tinted glass, ceramic, polymer, metal (e.g., aluminum, stainless steel (STS), or magnesium), or a combination of at least two thereof. The side surface 210C may be coupled to the front plate 201 and the back plate 207 and may be formed by a side bezel structure (or a side member) 206 including metal and/or polymer. According to another embodiment, the back plate 207 and the side bezel structure 206 may be integrally formed and may include the same material (e.g., a metal material such as aluminum). The fastening members 250 and 260 may be formed of various materials and shapes. A woven fabric, leather, rubber, urethane, metal, ceramic, or a combination of at least two thereof may be used to form it integrally and to allow a plurality of unit links to flow with each other.

According to an embodiment, the electronic device 200 may include at least one of a display 220 (refer to FIG. 3), audio modules 205 and 208, a sensor module 211, key input devices 202, 203, and 204, and a connector hole 209. According to another embodiment, the electronic device 200 may not include at least one of the foregoing components, for example, the key input devices 202, 203, and 204, the connector hole 209, or the sensor module 211, or additionally include another component.

The display 220 may be visually exposed through a substantial portion of the front plate 201, for example. The display 220 may be provided in a shape corresponding to a shape of the front plate 201, which may be various shapes such as a circle, an ellipse, or a polygon. The display 220 may be coupled to or disposed adjacent to a touch sensing circuit, a pressure sensor configured to measure the intensity (pressure) of a touch, and/or a fingerprint sensor.

The audio modules 205 and 208 may include a microphone hole 205 and a speaker hole 208. The microphone hole 205 may have therein a microphone for acquiring an external sound, and the microphone may be provided as a plurality of microphones to sense directions of a sound according to some embodiments. The speaker hole 208 may be used as an external speaker and a receiver for calls. According to another embodiment, the speaker hole 208 and the microphone hole 205 may be implemented as a single hole, or a speaker (e.g., a piezo speaker) may be included without the speaker hole 208.

The sensor module 211 may generate an electrical signal or a data value corresponding to an internal operating state of the electronic device 200 or an external environmental state. The sensor module 211 may include, for example, a biosensor module (i.e., sensor module 211) (e.g., a heart rate monitor (HRM)) disposed on the second surface 210B of the housing 210. The electronic device 200 may further include a sensor module (not shown), for example, at least one of an optical sensor, a motion sensor (e.g., a gyro sensor, an acceleration sensor, a speed sensor, etc.), a gesture sensor, a barometric pressure sensor, a magnetic sensor, a grip sensor, a color sensor, an infrared (IR) sensor, a biosensor, a temperature sensor, a humidity sensor, or an illuminance sensor.

The sensor module 211 may include electrode areas 213 and 214 that form a portion of the surface of the electronic device 200 and a biosignal detection circuit (not shown) electrically connected to the electrode areas 213 and 214. For example, the electrode areas 213 and 214 may include a first electrode area 213 and a second electrode area 214 disposed on the second surface 210B of the housing 210. The sensor module 211 may be configured such that the electrode areas 213 and 214 obtain an electrical signal from the body part of the user and the biosignal detection circuit detects biometric information of the user based on the electrical signal.

The key input devices 202, 203, and 204 may include a wheel key (i.e., key input device 202) disposed on the first surface 210A of the housing 210 and rotatable in at least one direction, and/or side key buttons (i.e., key input devices 203 and 204) disposed on the side surface 210C of the housing 210. The wheel key may be provided in a shape corresponding to the shape of the front plate 201. According to another embodiment, the electronic device 200 may not include some or all of the key input devices 202, 203, and 204, and the key input devices 202, 203, and 204 that are not included may be implemented in other forms such as soft keys on the display 220. The connector hole 209 may include another connector hole (not shown) that accommodates a connector (e.g., a universal serial bus (USB) connector) for transmitting and receiving power and/or data to and from an external electronic device and accommodates a connector for transmitting and receiving an audio signal to and from an external electronic device. The electronic device 200 may further include, for example, a connector cover (not shown) that covers at least a portion of the connector hole 209 and prevents an inflow of foreign substances into the connector hole 209.

The fastening members 250 and 260 may be detachably attached to at least a portion of the housing 210 using locking members 251 and 261. The fastening members 250 and 260 may include one or more of a fixing member 252, a fixing member fastening hole 253, a band guide member 254, and a band fixing ring 255.

The fixing member 252 may be configured to fix the housing 210 and the fastening members 250 and 260 to the body part (e.g., a wrist, an ankle, etc.) of the user. The fixing member fastening hole 253 may correspond to the fixing member 252 to fix the housing 210 and the fastening members 250 and 260 to the body part of the user. The band guide member 254 may be configured to limit a range of a movement of the fixing member 252 when the fixing member 252 is fastened to the fixing member fastening hole 253, so that the fastening members 250 and 260 are closely attached to the body part of the user. The band fixing ring 255 may limit a range of a movement of the fastening members 250 and 260 while the fixing member 252 and the fixing member fastening hole 253 are fastened to each other.

Referring to FIG. 3, an electronic device 300 (e.g., the electronic device 101 of FIG. 1 or the electronic device 200 of FIGS. 2A and 2B) may include a side bezel structure 310, a wheel key 320, a front plate 201, a display 220, a first antenna 350, a second antenna 355, a support member 360 (e.g., a bracket), a battery 370, a printed circuit board (PCB) 380, a sealing member 390, a back plate 393, and fastening members 395 and 397. At least one of the components of the electronic device 300 may be the same as or similar to at least one of the components of the electronic device 101 of FIG. 1 or the electronic device 200 of FIGS. 2A and 2B, and thus a repeated description thereof will be omitted here for brevity. The support member 360 may be disposed inside the electronic device 300 and connected to the side bezel structure 310, or be integrally formed with the side bezel structure 310. The support member 360 may be formed of, for example, a metal material and/or a non-metal material (e.g., polymer). The display 220 may be connected to one surface of the support member 360, and the PCB 380 may be connected to the other surface of the support member 360. The PCB 380 may be provided with a processor, a memory, and/or an interface. The processor may include, for example, one or more of a central processing unit (CPU), a graphics processing unit (GPU), an application processor, a sensor processor, or a communication processor.

The memory may include, for example, a volatile memory or a non-volatile memory. The interface may include, for example, a high-definition multimedia interface (HDMI), a USB interface, a secure digital (SD) card interface, and/or an audio interface. The interface may include, for example, a USB connector, an SD card/multimedia connect (MMC) connector, or an audio connector, to connect, electrically or physically, the electronic device 300 to an external electronic device.

The battery 370, which is a device for supplying power to at least one component of the electronic device 300, may include, for example, a non-rechargeable primary battery, a rechargeable secondary battery, or a fuel cell. For example, at least a portion of the battery 370 may be disposed on substantially the same plane as the PCB 380. The battery 370 may be disposed integrally inside the electronic device 300, or disposed detachably from the electronic device 300.

The first antenna 350 may be disposed between the display 220 and the support member 360. The antenna 350 may include, for example, a near-field communication (NFC) antenna, a wireless charging antenna, and/or a magnetic secure transmission (MST) antenna. For example, the first antenna 350 perform short-range communication with an external device, wirelessly transmit and receive power required for charging, or transmit a magnetism-based signal including a short-range communication signal or payment data. According to another embodiment, an antenna structure may be formed by a portion or combination of the side bezel structure 310 and/or the support member 360.

The second antenna 355 may be disposed between the PCB 380 and the back plate 393. The antenna 355 may include, for example, an NFC antenna, a wireless charging antenna, and/or an MST antenna. For example, the second antenna 355 may perform short-range communication with an external device, wirelessly transmit and receive power required for charging, or transmit a magnetism-based signal including a short-range communication signal or payment data. According to another embodiment, an antenna structure may be formed by a portion or combination of the side bezel structure 310 and/or the back plate 393.

The sealing member 390 may be disposed between the side bezel structure 310 and the back plate 393. The sealing member 390 may be configured to prevent moisture and foreign substances from flowing or entering into a space surrounded by the side bezel structure 310 and the back plate 393 from the outside.

According to various embodiments, an electronic device may be a device of one of various types. The electronic device may include, as non-limiting examples, a portable communication device (e.g., a smartphone, etc.), a computing device, a portable multimedia device, a portable medical device, a camera, a wearable device, or a home appliance. However, the electronic device is not limited to the foregoing examples.

It should be construed that various example embodiments of the disclosure and the terms used therein are not intended to limit the technological features set forth herein to some particular embodiments but include various changes, equivalents, or replacements of the example embodiments. In connection with the description of the drawings, like reference numerals may be used for similar or related components. As used herein, "A or B," "at least one of A and B," "at least one of A or B," "A, B, or C," "at least one of A, B, and C," and "A, B, or C," each of which may include any one of the items listed together in the corresponding one of the phrases, or all possible combinations thereof. Although terms of "first" or "second" are used to explain various components, the components are not limited to the terms. These terms should be used only to distinguish one component from another component. For example, a "first" component may be referred to as a "second" component, or similarly, and the "second" component may be referred to as the "first" component within the scope of the right according to the concept of the disclosure. It should also be understood that, when a component (e.g., a first component) is referred to as being "connected to" or "coupled to" another component with or without the term "functionally" or "communicatively," the component can be connected or coupled to the other component directly (e.g., wiredly), wirelessly, or via a third component.

As used in connection with various embodiments of the disclosure, the term "module" may include a unit implemented in hardware, software, or firmware, and may be interchangeably used with other terms, for example, "logic," "logic block," "part," or "circuitry." A module may be a single integral component, or a minimum unit or part thereof, adapted to perform one or more functions. For example, according to an embodiment, a module may be implemented in the form of an application-specific integrated circuit (ASIC).

Various embodiments set forth herein may be implemented as software (e.g., the program 140) including one or more instructions that are stored in a storage medium (e.g., the internal memory 136 or the external memory 138) that is readable by a machine (e.g., the electronic device 101). For example, a processor (e.g., the processor 120) of the machine (e.g., the electronic device 101) may invoke at least one of the one or more instructions stored in the storage medium, and execute it. This allows the machine to be operated to perform at least one function according to the at least one instruction invoked. The one or more instructions may include a code generated by a complier or a code executable by an interpreter. The machine-readable storage medium may be provided in the form of a non-transitory storage medium. The term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to various embodiments, a method according to an embodiment of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components or operations may be omitted, or one or more other components or operations may be added. Alternatively or additionally, a plurality of components (e.g., modules or programs) may be integrated into a single component. In such a case, according to various embodiments, the integrated component may perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

According to an embodiment, an electronic device (e.g., the electronic device 101 of FIG. 1, the electronic device 200 of FIG. 2A, or the electronic device 300 of FIG. 3) may include an optical sensor, a motion sensor, and/or a processor.

The optical sensor may include at least one light-emitting diode (LED) and a plurality of photodiodes. The optical sensor may be a sensor configured to emit, by the LED, light of a wavelength having a length in a specified range toward an object and detect light entering the photodiodes. The optical sensor may independently detect, from each of the photodiodes, light entering each of the photodiodes. The electronic device may select a type of LED (e.g., a green LED, a red LED, etc.) according to a biosignal of a user desired to be measured, and select a type of photodiode. For example, the electronic device may select an LED (e.g., a green LED) capable of stably detecting a signal even with a movement of a user and may emit light using the selected LED. For another example, the electronic device may detect a biosignal using a signal sensed from a photodiode having a highest measured signal strength.

The motion sensor may be a sensor configured to detect a motion of the electronic device and may include, for example, a position sensor, a displacement sensor, a speed sensor, an acceleration sensor, or a gyro sensor.

The processor may be an application processor or an auxiliary processor (e.g., a sensor hub). The processor may receive signals measured by the optical sensor and the motion sensor and store the received signals in the memory. The processor may determine wearing information of the electronic device by processing a biosignal of the user received from the photodiodes. When the electronic device is detected to be worn on the user, the processor may determine whether the user is exercising by using a signal received from the motion sensor. Hereinafter, the configuration and operations of the electronic device will be described in more detail.

Figure 4:
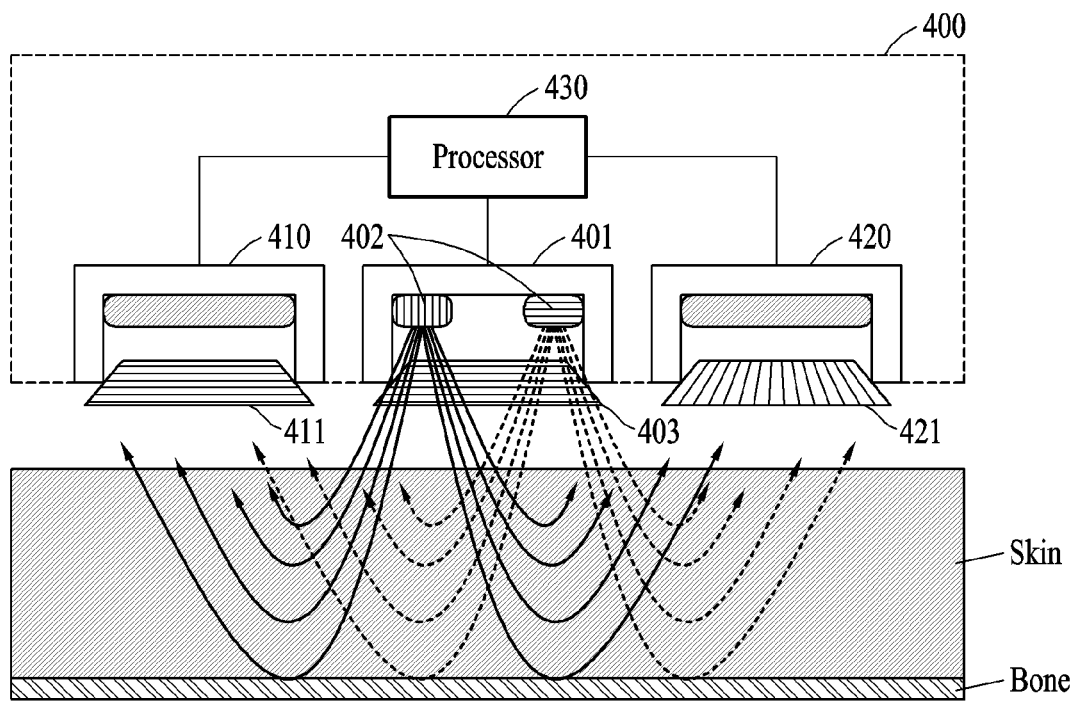
FIG. 4 is a diagram illustrating an example of operations of an electronic device according to an embodiment of the disclosure.

FIG. 4 is a diagram illustrating an example of operations of an electronic device according to an embodiment of the disclosure.

Referring to FIG. 4, an electronic device 400 (e.g., the electronic device 101 of FIG. 1) may include an optical sensor and a processor 430. The optical sensor (e.g., the sensor module 211 of FIG. 2B) may include an LED module 401 configured to emit light of a first polarization direction, a first photodiode 410, and a second photodiode 420.

The LED module 401 of the electronic device 400 may emit the light of the first polarization direction. The LED module 401 may include at least one LED 402 and a polarizer 403 of the first polarization direction that polarizes light emitted from the LED 402. For example, the polarizer 403 may be a polarizing film (e.g., a poly-vinyl-alcohol (PVA) film). For example, the LED 402 of the LED module 401 may include a green LED, a blue LED, a red LED, or an IR LED based on a wavelength range of the emitted light. Although the LED module 401 including at least one LED and a polarizer is mainly described herein, examples of which are not limited thereto. The LED module 401 may include at least one LED, and a polarizer may be disposed separately from the LED module 401.

The first photodiode 410 of the electronic device 400 may receive the light emitted from the LED module 401 through a first polarizer 411 having the first polarization direction. The first polarizer 411 of the first photodiode 410 may have the same first polarization direction as the polarizer 403 of the LED module 401. The second photodiode 420 of the electronic device 400 may receive the light emitted from the LED module 401 through a second polarizer 421 having a second polarization direction. The second polarization direction of the second polarizer 421 of the second photodiode 420 may be orthogonal to the first polarization direction of the polarizer 403 of the LED module 401.

The processor 430 of the electronic device 400 may determine wearing information of the electronic device 400 based on luminous intensity of light sensed from each of the first photodiode 410 and the second photodiode 420. Luminous intensity of light sensed by a photodiode may represent intensity of the received light. The wearing information may include information as to whether the electronic device 400 is worn and a wearing state of the electronic device 400. The information as to whether the electronic device 400 is worn may include whether the electronic device 400 is proximate to an object and whether the electronic device 400 is worn on a living object. The wearing state may include a first wearing state in which the electronic device 400 is tightly worn on a surface of a living object (e.g., a wrist) of a user, and a second wearing state in which the electronic device 400 is loosely worn against the surface (i.e., skin) of the living object of the user. Herein, the use of a living object of the user refers to any portion of a being that produces biological indicators that may be sensed or determined electronically. For example, the wrist, a torso legs, arms, neck, head or any other extremity of a body.

The first photodiode 410 and the second photodiode 420 may receive light having a polarization characteristic emitted from the LED module 401 by reflection. For example, the electronic device 400 may be worn on the living object (e.g., the skin) of the user. When the electronic device 400 is worn on the living object of the user, the LED module 401 may emit the light having the first polarization direction toward the living object of the user. The light emitted from the LED module 401 of the electronic device 400 may be reflected from the surface of the living object of the user or absorbed into the living object of the user. The light reflected from the surface of the living object may act as a noise component in measuring a pulse wave (e.g., photoplethysmogram (PPG)) signal.

The light emitted from the LED module 401 of the electronic device 400 and reflected from the surface of the living object of the user may retain an existing polarization characteristic. That is, the light having the first polarization direction after being emitted from the LED 402 and passing through the polarizer 403 may have the previous first polarization direction even though it is reflected from the surface of the living object of the user. The first photodiode 410 may receive light reflected from the surface of the living object of the user through the first polarizer 411, and the second photodiode 420 may also receive light reflected from the surface of the living object of the user through the second polarizer 421. The amount of the light received by the second photodiode 420 through the second polarizer 421 after being reflected from the surface of the living object may be smaller than the amount of the light received by the first photodiode 410 through the first polarizer 411 after being reflected from the surface of the living object. In contrast, the light emitted from the LED module 401 and absorbed into the living object of the user may gradually lose the polarization characteristic due to a scattering medium inside the living object and be dispersed in various polarization directions. For example, the light absorbed into the skin of the user may be scattered by the scattering medium and lose the previous polarization characteristic of the first polarization direction, and be reflected by the scattering medium inside the skin of the user to be incident on the first photodiode 410 and the second photodiode 420. The first photodiode 410 and the second photodiode 420 may receive light reflected from the inside of the living object of the user through the first polarizer 411 and the second polarizer 421, respectively.

The light emitted from the LED module 401 and reflected from the surface of the living object of the user may retain the polarization characteristic of the first polarization direction. The first photodiode 410 may receive light through the first polarizer 411 having the first polarization direction, and thus most of the light reflected from the surface of the living object of the user may enter the first photodiode 410 after passing through the first polarizer 411. In contrast, the second photodiode 420 may receive light through the second polarizer 421 having the second polarization direction perpendicular to the first polarization direction, and thus most of the light reflected from the surface of the living object of the user may not enter the second photodiode 420 because it does not pass through the second polarizer 421.

The light absorbed into the living object of the user after being emitted from the LED module 401 may lose the previous polarization characteristic of the first polarization direction by being scattered by the scattering medium in the living object, and have another polarization characteristic. Thus, the second photodiode 420 may receive a portion of the light that loses the previous polarization characteristic reflected from the inside of the living object through the second polarizer 421 having the second polarization direction. Similarly, the first photodiode 410 may also receive a portion of the light absorbed into the living object and reflected.

The first photodiode 410 may receive light through the first polarizer 411 of the first polarization direction, and thus light sensed from the first photodiode 410 may mainly indicate the light reflected from the surface of the living object. The second photodiode 420 may receive light through the second polarizer 421 of the second polarization direction, and thus light sensed from the second photodiode 420 may mainly indicate the light absorbed into the living object and reflected.

According to an embodiment, although not illustrated in FIG. 4, the optical sensor may further include at least one third photodiode that does not include a polarizer.

According to an embodiment, the electronic device 400 may further include at least one other component in addition to the components illustrated in FIG. 4. For example, the electronic device 400 may further include at least one (e.g., the communication module 190 or an input and output module (e.g., the display module 160, the input module 150, the sound output module 155, or the haptic module 179) of FIG. 1) of the components of the electronic device 101 illustrated in FIG. 1.

Figure 5:
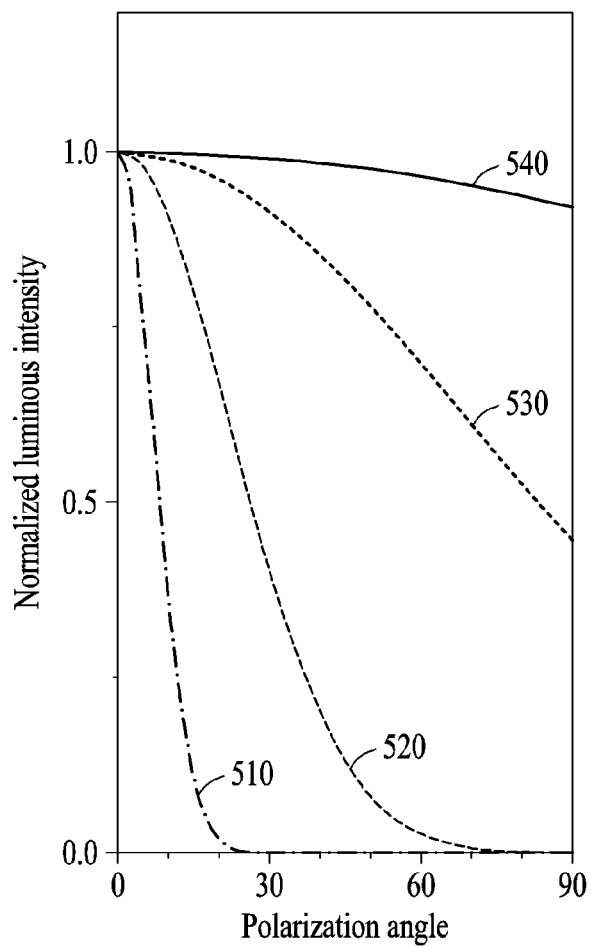
FIG. 5 is a graph illustrating an example of luminous intensity of light received by a photodiode based on a depth by which light emitted from a light-emitting diode (LED) module penetrates a living object (or a living body) according to an embodiment of the disclosure.

FIG. 5 is a graph illustrating an example of luminous intensity of light received by a photodiode based on a depth by which light emitted from an LED module penetrates a living object (or a living body) according to an embodiment of the disclosure.

Referring to FIG. 5, under the assumption that an electronic device (e.g., the electronic device 101 of FIG. 1 or the electronic device 400 of FIG. 4) is worn on a living object, a graph of luminous intensity of light that is reflected from a surface of the living object or reflected from the inside of the living object after being emitted from an LED module (e.g., the LED module 401 of FIG. 4) and is then sensed by a photodiode to which a polarizer having a polarization angle of 0 to 90 degrees)(° is applied may be obtained as illustrated in FIG. 5. A horizontal axis of the graph indicates a polarization angle of a polarizer applied to a photodiode with respect to a polarization direction of the light emitted from the LED module. The polarizer having the polarization angle of 0° may have the same polarization direction as the polarization direction of the light emitted from the LED module. The polarizer having the polarization angle of 90° may have a polarization direction perpendicular to the polarization direction of the light emitted from the LED module. A vertical axis of the graph indicates a normalized value of luminous intensity of light received by a photodiode having a polarizer having a different polarization angle based on luminous intensity of light received by the photodiode having the polarizer having the polarization angle of 0°.

A line 510 of the graph indicates luminous intensity of light received by a photodiode to which a polarizer is applied, when the light emitted from the LED module penetrates a living object by a depth of approximately 0.1 millimeters (mm) and is then reflected. Likewise, a line 520 of the graph indicates luminous intensity of light received by the photodiode to which the polarizer is applied, when the light penetrates the living object by a depth of approximately 0.5 mm and is then reflected. In addition, lines 530 and 540 of the graph indicate luminous intensities of light received by the photodiode to which the polarizer is applied, when the light penetrates the living object by depths of approximately 1.0 mm and 1.5 mm, respectively, and is then reflected. Referring to the graph illustrated in FIG. 5, when the depth of the living object by which light having a first polarization direction emitted from the LED module penetrates the living object of a user increases, luminous intensity of light sensed by a photodiode having a polarizer of a second polarization direction perpendicular to the first polarization direction may increase. This indicates that the light having the first polarization direction emitted from the LED module loses a previous polarization characteristic and has another polarization characteristic as it penetrates deeper the living object and scatters. According to an embodiment, an electronic device (e.g., the electronic device 400 of FIG. 4) may determine wearing information of the electronic device based on luminous intensity of light sensed from a first photodiode (e.g., the first photodiode 410 of FIG. 4) and luminous intensity of light sensed from a second photodiode (e.g., the second photodiode 420 of FIG. 4), which will be described in detail below with reference to FIGS. 6 through 10.

FIGS. 6 through 10 are flowcharts illustrating operations performed by an electronic device according to various embodiments of the disclosure.

Figure 6:
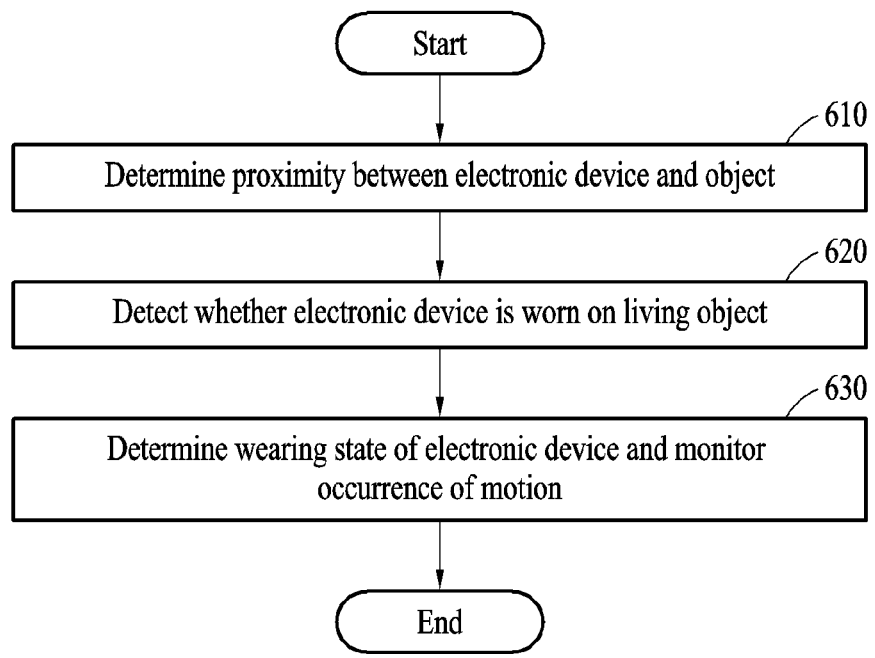
FIG. 6 is a flowchart illustrating an example of operations of determining wearing information of an electronic device by a processor of the electronic device according to an embodiment of the disclosure.

FIG. 6 is a flowchart illustrating an example of operations of determining wearing information of an electronic device by a processor of the electronic device according to an embodiment of the disclosure.

Referring to FIG. 6, in operation 610, a processor (e.g., the processor 120 of FIG. 1) of an electronic device (e.g., the electronic device 101 of FIG. 1 or the electronic device 400 of FIG. 4) may determine a proximity between the electronic device and an object. The object may include, for example, a living object (e.g., the skin of a user). The electronic device may determine the proximity between the electronic device and the object based on a ratio of luminous intensity of light sensed from a first photodiode (e.g., the first photodiode 410 of FIG. 4) to luminous intensity of light emitted from an LED module (e.g., the LED module 401 of FIG. 4).

In operation 620, the processor of the electronic device may detect whether the electronic device is worn on the living object. According to an embodiment, the electronic device may detect whether the electronic device is worn on the living object based on a form of a signal indicating luminous intensity of light sensed from a second photodiode (e.g., the second photodiode 420 of FIG. 4). According to another embodiment, the electronic device may detect whether the electronic device is worn on the living object based on a ratio of the luminous intensity of the light sensed from the first photodiode to the luminous intensity of the light sensed from the second photodiode.

In operation 630, the processor of the electronic device may determine a wearing state of the electronic device and monitor whether a motion occurs. According to an embodiment, when the electronic device is detected to be worn on the living object, the processor of the electronic device may determine the wearing state of the electronic device by comparing the luminous intensity of the light sensed from the first photodiode and the luminous intensity of the light sensed from the second photodiode. For example, the processor of the electronic device may determine whether the wearing state is a first wearing state in which the electronic device is tightly worn on the living object of the user or a second wearing state in which the electronic device is loosely worn on the living object of the user. In addition, while the electronic device is in the second wearing state, the processor of the electronic device may additionally monitor whether a motion occurs. For example, the electronic device may monitor whether a motion of the electronic device occurs based on a change in the luminous intensity of the light sensed from the second photodiode. For another example, the electronic device may additionally use a motion sensor (not shown) configured to monitor whether a motion occurs.

Figure 7:
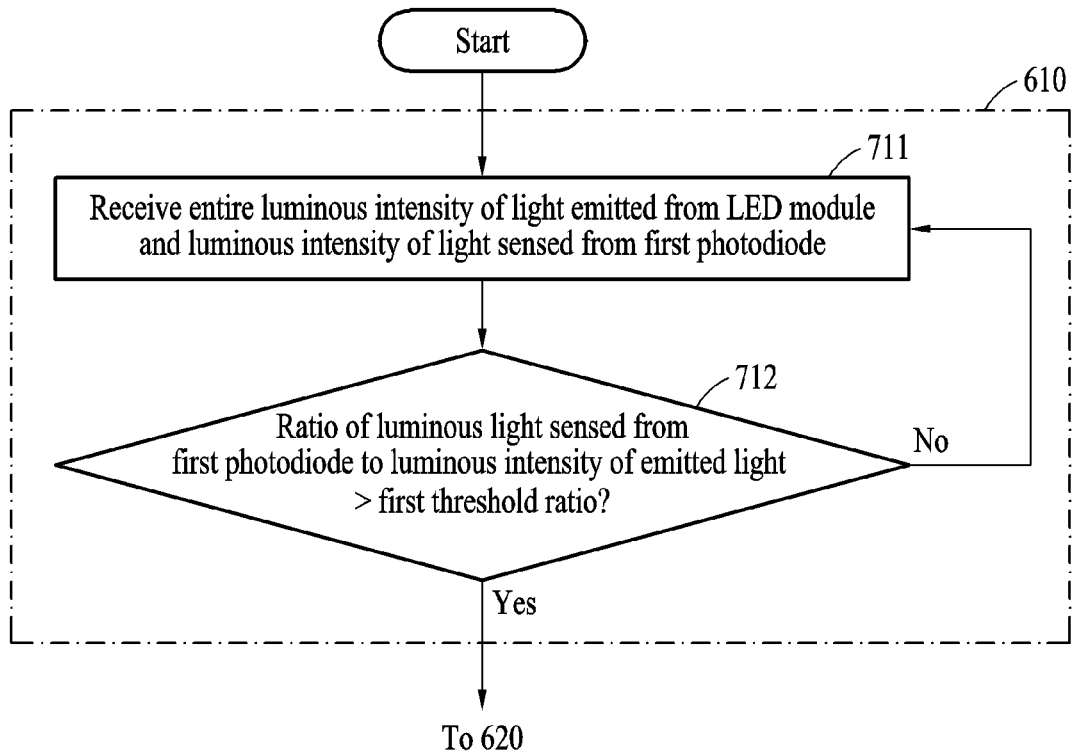
FIG. 7 is a flowchart illustrating an example of operations of determining proximity between an electronic device and an object by a processor of the electronic device according to an embodiment of the disclosure.

FIG. 7 is a flowchart illustrating an example of operations of determining proximity between an electronic device and an object by a processor of the electronic device according to an embodiment of the disclosure.

Referring to FIG. 7, operation 610 described above with reference to FIG. 6 will be described in detail. In operation 711, a processor (e.g., the processor 120 of FIG. 1) of an electronic device (e.g., the electronic device 101 of FIG. 1 or the electronic device 400 of FIG. 4) may receive an entire luminous intensity of light emitted from an LED module (e.g., the LED module 401 of FIG. 4) and the luminous intensity of light sensed from a first photodiode (e.g., the first photodiode 410 of FIG. 4). In operation 712, the processor of the electronic device may calculate a first ratio of the luminous intensity of the light sensed from the first photodiode to the luminous intensity of the light emitted from the LED module, and determine proximity between the electronic device and an object based on the first ratio.

According to an embodiment, it is assumed that the LED module of the electronic device emits light of a first polarization direction toward an object. The first photodiode may receive light through a first polarizer (e.g., the first polarizer 411 of FIG. 4) having the first polarization direction, and may thus sense light that retains a previous polarization characteristic after being reflected mainly from a surface of the object. The electronic device may estimate an amount of light reflected from the surface of the object using the luminous intensity of the light sensed from the first photodiode. For example, when the luminous intensity of the light sensed from the first photodiode is relatively high compared to the luminous intensity of the emitted light, the electronic device may determine a distance between the electronic device and the object to be short. When the luminous intensity of the light sensed from the first photodiode is relatively low compared to the luminous intensity of the emitted light, the electronic device may determine the distance between the electronic device and the object to be great. When the distance between the electronic device and the object decreases, an amount of light reflected from the surface of the object after being emitted from the LED module may increase. In response to the first ratio being greater than a first threshold ratio, the processor of the electronic device may determine that the electronic device and the object may be proximate to each other. In response to the first ratio being less than the first threshold ratio, the processor of the electronic device may determine that there is no object proximate to the electronic device within a certain distance. The first threshold ratio may be a ratio that is set based on the luminous intensity of the light emitted from the LED module to determine whether the electronic device is proximate to the object. For example, the first threshold ratio may be set based on a direct current (DC) threshold value which is a reference output used for a PPG sensor to determine the proximity to the object. When it is determined that there is no object proximate to the electronic device, the electronic device may continuously determine the proximity between the electronic device and the object by receiving the entire luminous intensity of the light emitted from the LED module and the luminous intensity of the light sensed from the first photodiode each preset period.

Although whether the electronic device is proximate to an object may be determined using only the luminous intensity of the light sensed from the first photodiode, whether the proximate object is a living object may not be readily determined. When it is determined that the electronic device and the object are proximate to each other, the processor of the electronic device may determine whether the object proximate to the electronic device is a living object in operation 620. Whether the object proximate to the electronic device is a living object may be determined through operations to be described below with reference to FIG. 8.

Figure 8:
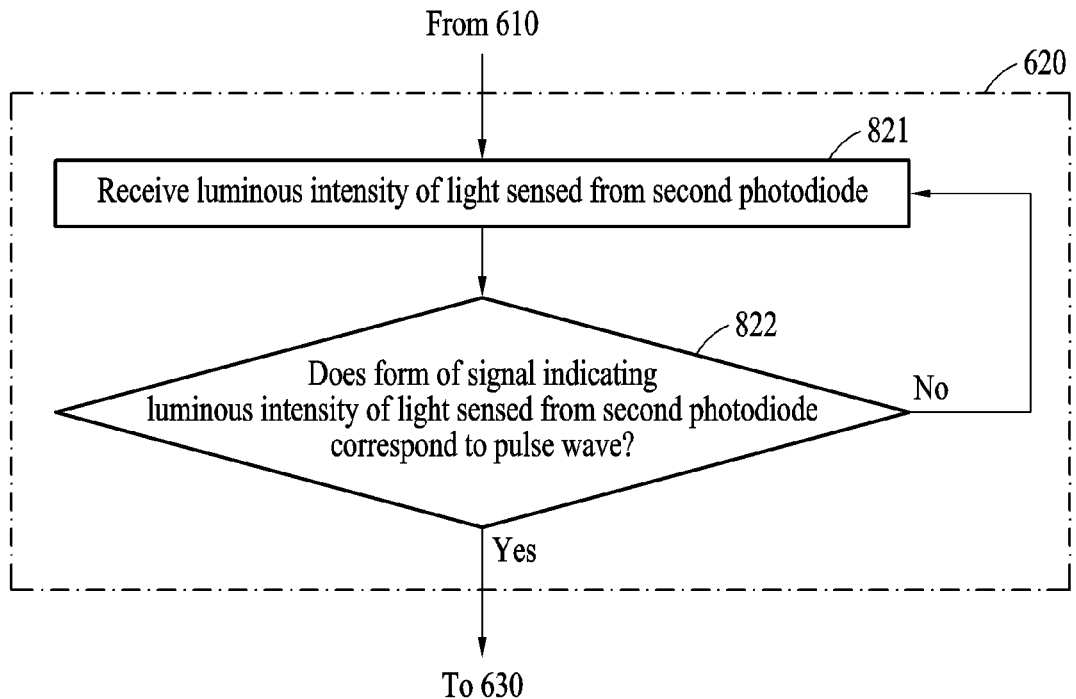
FIG. 8 is a flowchart illustrating an example of operations of determining whether an electronic device is worn on a living object by a processor of the electronic device according to an embodiment of the disclosure.

FIG. 8 is a flowchart illustrating an example of operations of determining whether an electronic device is worn on a living object by a processor of the electronic device according to an embodiment of the disclosure.

Referring to FIG. 8, operation 620 described above with reference to FIG. 6 will be described in detail. In operation 821, a processor (e.g., the processor 120 of FIG. 1) of an electronic device (e.g., the electronic device 101 of FIG. 1 or the electronic device 400 of FIG. 4) may receive luminous intensity of light sensed from a second photodiode (e.g., the second photodiode 420 of FIG. 4). In operation 822, the processor may detect whether the electronic device is worn on a living object based on a form of a signal indicating the luminous intensity of the light sensed from the second photodiode. When the form of the signal indicating the luminous intensity of the light sensed from the second photodiode corresponds to the form of a pulse wave, the processor may detect that the electronic device is worn on the living object. The pulse wave may indicate a recording of pulsation of thoracic walls and great vessels by heartbeats as a waveform.

According to an embodiment, under the assumption that the electronic device is worn on the living object (e.g., the skin of a user), an LED module (e.g., the LED module 401 of FIG. 4) of the electronic device may emit light of a first polarization direction toward an object. The second photodiode may receive light through a second polarizer (e.g., the second polarizer 421 of FIG. 4) having a second polarization direction perpendicular to the first polarization direction, and may thus receive light that loses a previous polarization characteristic by being mostly absorbed into the living object of the user and reflected by a scattering medium. When the light emitted from the LED module is absorbed into the living object of the user, the blood vessels inside the living object may also contract and dilate repeatedly as the heart of the user contracts and dilates, and an amount of red blood cells in the living object may increase and decrease repeatedly with time. The light absorbed into the living object of the user after being emitted from the LED module may change in an amount reflected in the living object over time according to the increase and decrease in the amount of the red blood cells in the living object. An amount of the light entering the second photodiode may have a form of a pulse wave. When a form of a signal indicating the luminous intensity of the light sensed from the second photodiode has the form of the pulse wave, the processor of the electronic device may determine that the electronic device is worn on the living object. However, when the form of the signal indicating the luminous intensity of the light sensed from the second photodiode does not have the form of the pulse wave, the processor of the electronic device may determine an object proximate to the electronic device not to be the living object. When the processor of the electronic device determines the object proximate to the electronic device to be an object that is not the living object, the processor may continuously detect whether the electronic device is worn on the living object by receiving luminous intensity of light sensed from the second photodiode at preset intervals.

However, a method of determining whether the electronic device is worn on the living object is not limited to the method described above. According to another embodiment, the electronic device may detect whether the electronic device is worn on the living object based on luminous intensity of light sensed from the first photodiode and luminous intensity of light sensed from the second photodiode. The processor of the electronic device may detect whether the electronic device is worn on the living object by calculating a second ratio that is a ratio of the luminous intensity of the light sensed from the first photodiode to the luminous intensity of the light sensed from the second photodiode. The electronic device may calculate the second ratio as represented by Equation 1 below.

$$\text{Second ratio} = \frac{\text{Luminous intensity of light sensed from first photodiode}}{\text{Luminous intensity of light sensed from second photodiode}} \quad \text{Equation 1}$$

When the electronic device is worn on the living object, light reflected through scattering inside the living object may be sensed by the second photodiode. In contrast, when the electronic device is worn on an object that is not the living object, a phenomenon in which light is absorbed into the living object and scattered by a scattering medium may not occur and there may be almost no light entering the second photodiode. Thus, when the electronic device is worn on an object that is not the living object, a relatively high second ratio may be calculated compared to when the electronic device is worn on the living object, and thus the electronic device may detect whether the electronic device is worn on the living object based on this second ratio.

Figure 9:
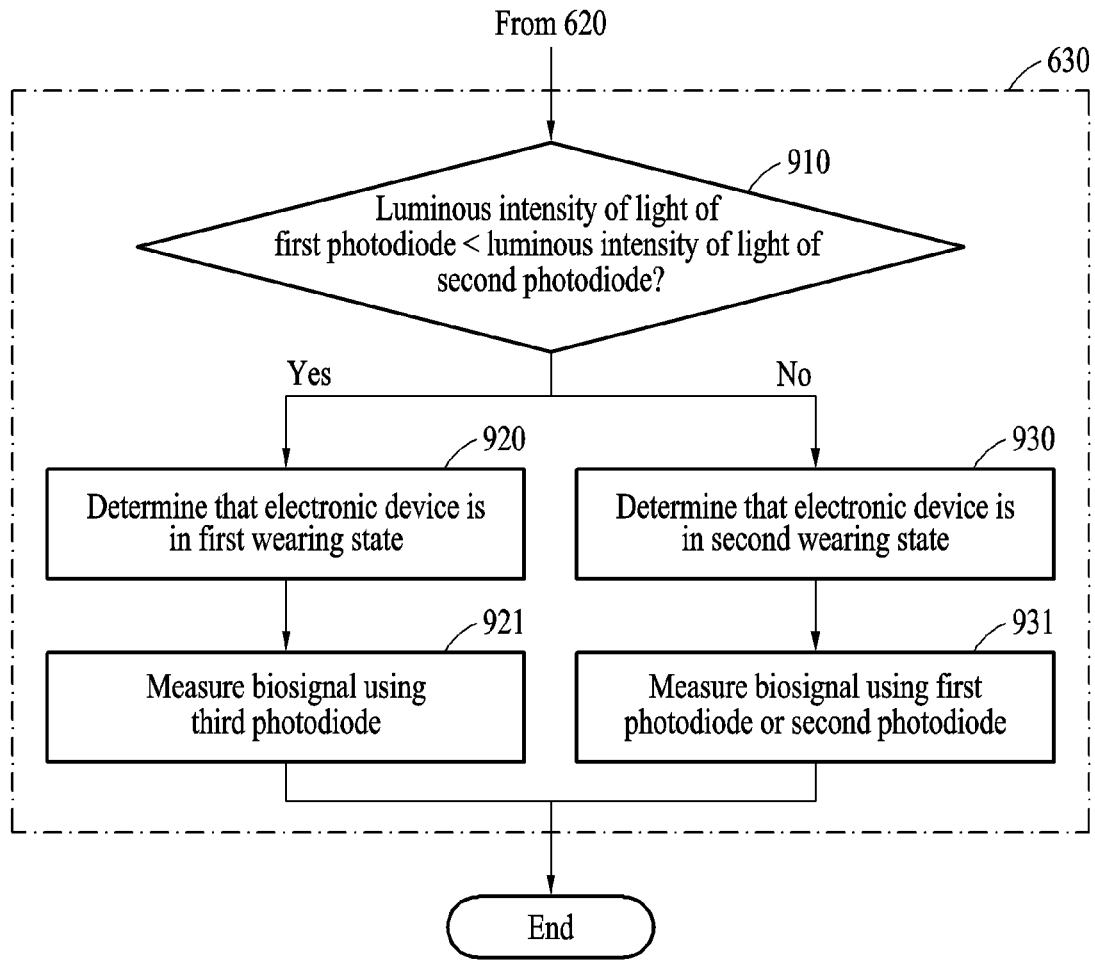
FIG. 9 is a flowchart illustrating an example of operations of determining a wearing state of an electronic device by a processor of the electronic device according to an embodiment of the disclosure.

FIG. 9 is a flowchart illustrating an example of operations of determining a wearing state of an electronic device by a processor of the electronic device according to an embodiment of the disclosure.

Referring to FIG. 9, operation 630 described above with reference to FIG. 6 will be described in detail. In operation 910, when a processor (e.g., the processor 120 of FIG. 1) of an electronic device (e.g., the electronic device 101 of FIG. 1 or the electronic device 400 of FIG. 4) detects that the electronic device is worn on a living object, the processor may determine a wearing state of the electronic device by comparing luminous intensity of light sensed from a first photodiode (e.g., the first photodiode 410 of FIG. 4) and luminous intensity of light sensed from a second photodiode (e.g., the second photodiode 420 of FIG. 4).

In operation 920, when the luminous intensity of the light sensed from the first photodiode is less than the luminous intensity of the light sensed from the second photodiode ("Yes" in operation 910), the processor may determine the wearing state of the electronic device to be a first wearing state in which the electronic device is tightly worn on the living object of a user. According to an embodiment, when a second ratio that is a ratio of the luminous intensity of the light sensed from the first photodiode to the luminous intensity of the light sensed from the second photodiode is less than a second threshold ratio, the electronic device may determine that the electronic device is in the first wearing state. The second threshold ratio may be approximately 1/10, for example, but is not limited thereto.

When the electronic device is determined to be in the first wearing device in which the electronic device is tightly worn on the living object, a three-dimensional (3D) tilt angle between a polarizer of an LED module and a polarizer of a photodiode may be small, and thus an amount of light entering the photodiode after being reflected from a surface of the living object may be small. Similarly, when the electronic device is in the first wearing state, an angle between the electronic device and the surface of the living object may be small, and thus an amount of light entering the photodiode after being reflected from the surface of the living object may be small.

When the electronic device is in the first wearing state, an amount of light entering the photodiode after being absorbed into the living object and then reflected may be relatively greater than the amount of the light entering the photodiode after being reflected from the surface of the living object. The first photodiode may sense mainly the light reflected from the surface of the living object, and the second photodiode may sense mainly the light reflected after being absorbed into the living object. When the luminous intensity of the light sensed from the second photodiode is greater than the luminous intensity of the light sensed from the first photodiode, the processor of the electronic device may determine that the electronic device is in the first wearing state.

In operation 930, when the luminous intensity of the light sensed from the first photodiode is greater than or equal to the luminous intensity of the light sensed from the second photodiode ("No" in operation 910), the processor may determine that the electronic device is in a second wearing state in which the electronic device is loosely worn on the living object. According to an embodiment, when the calculated second ratio is greater than a third threshold ratio, the electronic device may determine that the electronic device is in the second wearing state. The third threshold ratio may be approximately 10, for example, but is not limited thereto.

When the electronic device is in the second wearing state in which the electronic device is loosely worn on the living object, the 3D tilt angle between the polarizer of the LED module and the polarizer of the photodiode may increase, and thus an amount of light entering the photodiode by being reflected from the surface of the living object may increase. Similarly, when the electronic device is in the second wearing state, the angle between the electronic device and the surface of the living object may increase, and thus an amount of light entering the photodiode by being reflected from the surface of the living object may increase. When the electronic device is in the second wearing state, an amount of light entering the photodiode by being reflected from the inside of the living object may be relatively smaller than an amount of light entering the photodiode by being reflected from the surface of the living object. The first photodiode may receive mainly the light reflected from the surface of the living object, and thus the processor of the electronic device may determine that the electronic device is in the second wearing state when the luminous intensity of the light sensed from the first photodiode is greater than the luminous intensity of the light sensed from the second photodiode.

According to an embodiment, the processor of the electronic device may select a type of a photodiode for measuring a biosignal based on the determined wearing state. The processor of the electronic device may more accurately measure a biosignal of a user by using only a signal sensed by the photodiode of the selected type.

In operation 921, when the electronic device is determined to be in the first wearing state, the processor of the electronic device may determine, to be the photodiode for measuring the biosignal of the user, a third photodiode configured to receive light reflected from the surface or the inside of the living object without a polarizer. The processor of the electronic device may then measure the biosignal of the user using the third photodiode. For example, the processor of the electronic device may measure the biosignal of the user by obtaining a signal sensed by the third photodiode. In a case of the polarizer, light incidence transmittance may be approximately 50%, and thus a light loss may occur when the photodiode receives light through the polarizer. Thus, when the electronic device is determined to be in the first wearing state in which the electronic device is tightly worn on the living object of the user, the electronic device may obtain the biosignal having improved sensed intensity by measuring the biosignal of the user using the third photodiode without the polarizer.

In operation 931, when the electronic device is determined to be in the second wearing state, the processor of the electronic device may select one from between the first photodiode and the second photodiode to be the photodiode for measuring the biosignal of the user. When the electronic device is in the second wearing state, the processor of the electronic device may select one of the first photodiode and the second photodiode based on whether a motion occurs to measure the biosignal of the user. The electronic device may measure the biosignal of the user by selecting one of the first photodiode and the second photodiode based on whether the motion occurs through operations to be described hereinafter with reference to FIG. 10.

Figure 10:
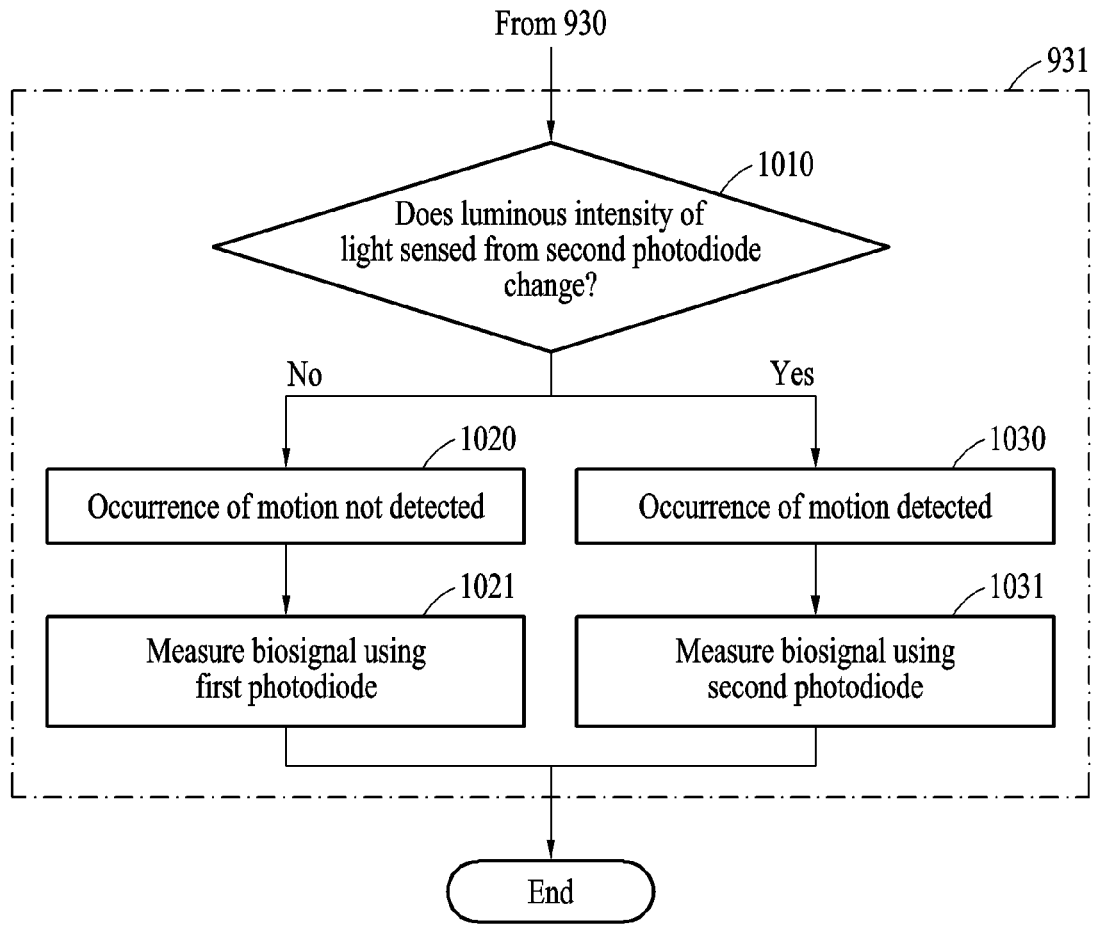
FIG. 10 is a flowchart illustrating an example of operations of detecting whether a motion occurs when an electronic device is in a second wearing state according to an embodiment of the disclosure.

FIG. 10 is a flowchart illustrating an example of operations of detecting whether a motion occurs when an electronic device is in a second wearing state according to an embodiment of the disclosure.

Referring to FIG. 10, hereinafter, operation 931 described above with reference to FIG. 9 will be described in detail. In operation 1010, a processor (e.g., the processor 120 of FIG. 1) of an electronic device (e.g., the electronic device 101 of FIG. 1 or the electronic device 400 of FIG. 4) may monitor whether a motion of the electronic device occurs while the electronic device is in a second wearing state. For example, the processor may monitor whether the motion of the electronic device occurs based on a change in luminous intensity of light sensed from a second photodiode (e.g., the second photodiode 420 of FIG. 4). For another example, the processor may monitor whether the motion of the electronic device occurs based on a value sensed by a motion sensor.

In operation 1020, when there is no change in the luminous intensity of the light sensed from the second photodiode, the processor may determine that the motion is not detected. According to an embodiment, when the luminous intensity of the light sensed from the second photodiode is consistently maintained, the processor of the electronic device may determine that the motion is not detected from the electronic device. When the luminous intensity of the light sensed from the second photodiode is consistent, the processor may determine that the motion does not occur in the electronic device. According to another embodiment, when a change rate of the luminous intensity of the light sensed from the second photodiode is less than a threshold change rate, the processor may determine that the motion is not detected from the electronic device.

In operation 1030, when there is a change in the luminous intensity of the light sensed from the second photodiode, the processor may determine that the motion is detected. According to an embodiment, when the luminous intensity of the light sensed from the second photodiode is not consistently maintained, the processor may determine that the motion is detected from the electronic device. When the luminous intensity of the light sensed from the second photodiode is not consistently maintained, the processor may determine that the motion occurs in the electronic device. According to another embodiment, when the change rate of the luminous intensity of the light sensed from the second photodiode is greater than or equal to the threshold change rate, the processor of the electronic device may detect the motion from the electronic device.

According to an embodiment, when the electronic device is in the second wearing state, the processor of the electronic device may select a type of a photodiode for measuring a biosignal of a user based on whether a motion occurs. The processor of the electronic device may measure the biosignal of the user using a signal sensed by the photodiode of the selected type.

In operation 1021, when the electronic device is in the second wearing state and the motion is not detected to occur, the processor may select a first photodiode (e.g., the first photodiode 410) to measure the biosignal of the user. The processor may measure the biosignal of the user by obtaining a signal sensed by the selected first photodiode.

In operation 1031, when the electronic device is in the second wearing state and the motion is detected to occur, the processor may select a second photodiode to measure the biosignal of the user. The processor may measure the biosignal of the user by obtaining a signal sensed by the selected second photodiode.

According to an embodiment, the electronic device may select a photodiode based on at least one of or a combination of two or more of a wearing state of the electronic device and whether a motion occurs and measure a biosignal using a signal sensed by the selected photodiode, thereby reducing the inaccuracy of the biosignal.

For example, when a motion of the electronic device being in the second wearing state is not detected, the processor of the electronic device may measure a biosignal of a user by using the first photodiode that senses light with greater luminous intensity than that of light sensed by the second photodiode.

For another example, when the motion of the electronic device being in the second wearing state is detected, the processor of the electronic device may measure a biosignal of the user by activating only the second photodiode having a second polarizer of a second polarization direction robust against motion artifact. When the motion of the electronic device occurs, a signal measured by the first photodiode that receives mainly light reflected from a surface of a living object may include external noise. The electronic device may measure a biosignal of the user through the second photodiode, excluding the first photodiode from the measurement of the living object, thereby increasing the efficiency in the measurement of the living object.

For example, when a general optical sensor measures a heartbeat signal during an exercise of the user, the heartbeat signal measured by the optical sensor may actually include a noise component reflected from the skin, in addition to the heartbeat signal, due to a motion of the electronic device. However, according to an embodiment, the electronic device may remove the noise component reflected from the surface (e.g., the skin) of the living object by excluding the signal measured by the first photodiode. That is, when a motion of the electronic device occurs, the electronic device may activate only the second photodiode and measure a heartbeat signal of the user more accurately.

According to an embodiment, the processor of the electronic device may determine wearing information of the electronic device at preset intervals. The processor of the electronic device may determine the wearing information of the electronic device by receiving luminous intensity of light sensed from each of the first photodiode and the second photodiode, through operations described above with reference to FIGS. 6 through 10.

Figure 11:
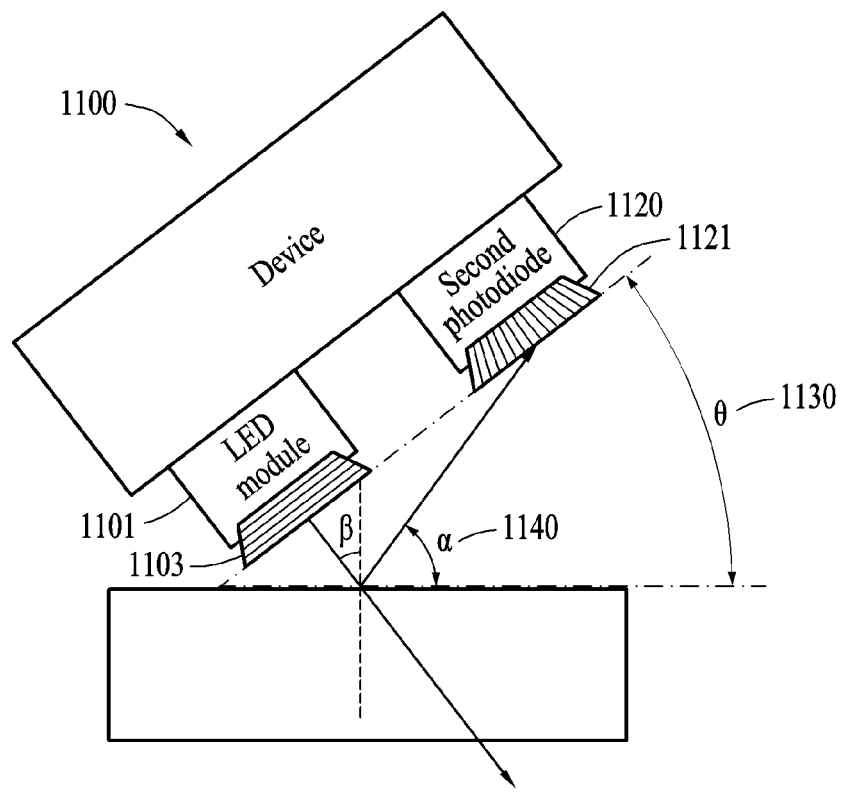
FIG. 11 is a diagram illustrating an example of a change in a tilt angle between a polarizer of an LED module and a second polarizer of a second photodiode by the occurrence of a motion of an electronic device according to an embodiment of the disclosure.

FIG. 11 is a diagram illustrating an example of a change in a tilt angle between a polarizer of an LED module and a second polarizer of a second photodiode by the occurrence of a motion of an electronic device according to an embodiment of the disclosure.

Referring to FIG. 11, according to an embodiment, under the assumption that an electronic device 1100 (e.g., the electronic device 101 of FIG. 1 or the electronic device 400 of FIG. 4) is worn on a living object of a user, an angle θ 1130 between the electronic device 1100 and a surface of the living object of the user may gradually increase when a motion of the electronic device 1100 increases. A 3D tilt angle between a polarizer 1103 having a first polarization direction of an LED module 1101 and a second polarizer 1121 having a second polarization direction perpendicular to the first polarization direction may be an angle α 1140 between light emitted from the LED module 1101 and reflected from the surface of the living object and the surface of the skin. When the motion of the electronic device 1100 increases, the angle α 1140 between the light reflected from the surface of the living object and the surface of the living object may increase, and thus the tilt angle α between the polarizer 1103 of the LED module 1101 and the second polarizer 1121 of the second photodiode 1120 may also increase.

According to an embodiment, when the motion occurs in the electronic device 1100, the second photodiode 1120 of the electronic device 1100 may receive light through an optical path changed by the 3D tilt angle changed between the polarizer 1103 of the LED module 1101 and the second polarizer 1121 of the second photodiode 1120. Luminous intensity of light reflected from the surface of the living object of the user and sensed by the second photodiode 1120 based on the tilt angle between the polarizer 1103 of the LED module 1101 and the second polarizer 1121 of the second photodiode 1120 may be determined by luminous intensity of light reflected from the surface of the living object and input to the second polarizer 1121, the tilt angle α between the polarizer 1103 of the LED module 1101 and the second polarizer 1121 of the second photodiode 1120, an incidence angle β of light with respect to the surface of the living object, and transmittance of light input to the second photodiode 1120 through the second polarizer 1121.

When the motion occurs in the electronic device 1100, the 3D tilt angle α 1140 between the polarizer 1103 of the LED module 1101 and the second polarizer 1121 of the second photodiode 1120 may change, and an amount of light reflected from the surface of the living object and input to the second photodiode 1120 may change due to the change in the tilt angle α 1140. Thus, a processor of the electronic device 1100 may determine whether the motion of the electronic device 1100 occurs based on a change in the luminous intensity of the light sensed from the second photodiode 1120. For example, when the change in the luminous intensity of the light sensed from the second photodiode 1120 is greater than or equal to a threshold change rate, the processor of the electronic device 1100 may determine that the motion occurs in the electronic device 1100.

Figure 12:
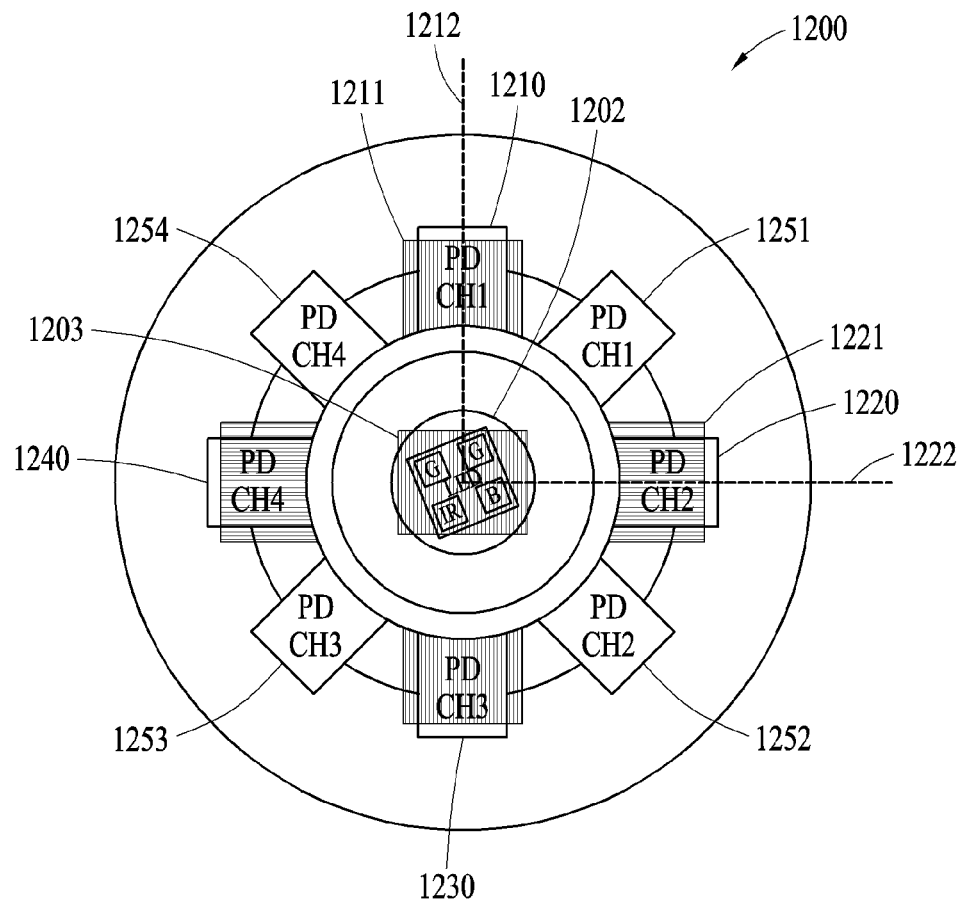
FIG. 12 is a diagram illustrating an example arrangement of an optical sensor in an electronic device according to an embodiment of the disclosure.

FIG. 12 is a diagram illustrating an example arrangement of an optical sensor in an electronic device according to an embodiment of the disclosure.

According to an embodiment, an optical sensor of an electronic device 1200 (e.g., the electronic device 101 of FIG. 1) may include an LED module 1202, a first photodiode 1210, and a second photodiode 1220. The optical sensor of the electronic device 1200 may receive, through a photodiode, light reflected from a surface of a living object of a user or absorbed into the living object and then reflected after being emitted from the LED module 1202, and measure a biosignal of the user. A processor (not shown) of the electronic device 1200 may measure biometric information of the user using a signal sensed from the photodiode. For example, the electronic device 1200 may measure various types of biometric information, such as, for example, heart rate, stress, saturation of partial pressure oxygen (SpO2), blood sugar, and blood pressure.

The LED module 1202 may include at least one LED (e.g., a red LED, a green LED, etc.) and a polarizer 1203 of a first polarization direction for emitting light of the first polarization direction. The first photodiode 1210 may receive reflected light through a first polarizer 1211 of the first polarization direction identical to the polarization direction of the light emitted from the LED module 1202. The second photodiode 1220 may receive reflected light through a second polarizer 1221 of a second polarization direction perpendicular to the first polarization direction.

The first photodiode 1210 and the second photodiode 1220 may be arranged based on the LED module 1202 such that an imaginary line 1212 connecting the first photodiode 1210 and the LED module 1202 and an imaginary line 1222 connecting the second photodiode 1220 and the LED module 1202 are perpendicular to each other.

In addition, the first photodiode 1210, the second photodiode 1220, and additional photodiodes 1230 and 1240 may be individually arranged at positions at which distances therebetween are maximized on one surface in a limited form factor of the electronic device 1200.

According to an embodiment, the electronic device 1200 may include at least one photodiode that receives light through a first polarizer of a first polarization direction.

Referring to FIG. 12, the electronic device 1200 may further include the additional photodiode 1230 that receives light through the first polarizer of the first polarization direction. The first photodiode 1210 and the additional photodiode 1230 having the same first polarization direction may be arranged at positions at which a distance therebetween is maximized on one surface of the electronic device 1200. On a plane on which the first photodiode 1210 is arranged, the additional photodiode 1230 may be arranged on an opposite side of the first photodiode 1210 with respect to the LED module 1202. For example, the additional photodiode 1230 may be arranged at a position symmetrical to that of the first photodiode 1210 with respect to the LED module 1202.

According to an embodiment, the electronic device 1200 may include at least one photodiode that receives light through a second polarizer of a second polarization direction perpendicular to the first polarization direction. For example, the electronic device 1200 may further include the additional photodiode 1240 that receives light through the second polarizer of the second polarization direction. The second photodiode 1220 and the additional photodiode 1240 having the same second polarization direction may be arranged at positions at which a distance therebetween is maximized on one surface of the electronic device 1200. On a plane on which the second photodiode 1220 is arranged, the additional photodiode 1240 may be arranged on an opposite side of that of the second photodiode 1220 with respect to the LED module 1202. For example, the additional photodiode 1240 may be arranged at a position symmetrical to that of the second photodiode 1220 with respect to the LED module 1202.

In addition to the additional photodiodes 1230 and 1240, the electronic device 1200 may further include one or more third photodiodes 1251, 1252, 1253, and 1254 that receive the light emitted from the LED module 1202 without a polarizer.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device, comprising:
   a lighting-emitting diode (LED) configured to emit light of a first polarization direction;
   a first photodiode configured to receive the light emitted from the LED through a first polarizer having the first polarization direction;
   a second photodiode configured to receive the light emitted from the LED through a second polarizer having a second polarization direction perpendicular to the first polarization direction;
   a third photodiode configured to receive the light emitted from the LED without a polarizer;
   at least one processor; and
   memory storing instructions, that when executed by the at least one processor, cause the electronic device to:
   determine whether the electronic device is worn on a living object, based on luminous intensity of light sensed from each of the first photodiode and the second photodiode,
      in response to determining that the electronic device is worn on the living object, determine, a wearing state of the electronic device representing a degree of tightness with which the electronic device is worn on the living object, to be one of a first wearing state indicating a first degree of tightness or a second wearing state indicating a second degree of tightness, based on the luminous intensity of the light sensed from the first photodiode and the luminous intensity of the light sensed from the second photodiode, wherein the first degree of tightness is greater than the second degree of tightness,
      in response to determining the wearing state of the electronic device to be the second wearing state, monitor whether a motion of the electronic device occurs based on a change in the luminous intensity of the light sensed from the second photodiode,
      select a photodiode among from the first photodiode, the second photodiode, and the third photodiode, based on at least one of the wearing state of the electronic device or occurrence of motion, and
      measure a biosignal using a signal sensed by the selected photodiode.

2. The electronic device of claim 1, wherein the instructions, when executed by the at least one processor, cause the electronic device to:
   determine proximity between the electronic device and the living object based on a ratio of the luminous intensity of the light sensed from the first photodiode to luminous intensity of the light emitted from the LED.

3. The electronic device of claim 1, wherein the instructions, when executed by the at least one processor, cause the electronic device to:
   determine that the electronic device is worn on the living object, in response to a signal indicating the luminous intensity of the light sensed from the second photodiode having a form of a pulse wave.

4. The electronic device of claim 3, wherein the instructions, when executed by the at least one processor, cause the electronic device to:
   in response to determining that the electronic device is worn on the living object, determine the wearing state of the electronic device by comparing the luminous intensity of the light sensed from the first photodiode and the luminous intensity of the light sensed from the second photodiode.

5. The electronic device of claim 1, wherein the instructions, when executed by the at least one processor, cause the electronic device to:
in response to determining that the electronic device is worn on the living object, calculate a ratio of the luminous intensity of the light sensed from the first photodiode to the luminous intensity of the light sensed from the second photodiode,
in response to the ratio being less than a threshold ratio, determine the wearing state of the electronic device to be the first wearing state, and
in response to the ratio being greater than other threshold ratio greater than the threshold ratio, determine the wearing state of the electronic device to be the second wearing state.

6. The electronic device of claim 1, wherein the instructions, when executed by the at least one processor, cause the electronic device to:
measure the biosignal using only the signal sensed by the selected photodiode, and
exclude, from measuring the biosignal, a signal sensed by the other photodiode different from the selected photodiode of the first photodiode, the second photodiode, and the third photodiode.

7. The electronic device of claim 1, wherein the instructions, when executed by the at least one processor, cause the electronic device to:
determine whether the electronic device is worn on the living object or the wearing state of the electronic device receiving the luminous intensity of the light sensed from each of the first photodiode and the second photodiode at preset intervals.

8. The electronic device of claim 1,
wherein the first photodiode and the second photodiode are arranged with respect to the LED such that an imaginary line connecting the first photodiode and the LED, and an imaginary line connecting the second photodiode and the LED are perpendicular to each other.

9. The electronic device of claim 1,
wherein the instructions, when executed by the at least one processor, cause the electronic device to:
in response to determining the wearing state of the electronic device to be the first wearing state, select the third photodiode as the selected photodiode and measure the biosignal using a signal sensed by the third photodiode.

10. The electronic device of claim 1, wherein the instructions, when executed by the at least one processor, cause the electronic device to:
in response to determining the wearing state of the electronic device to be the second wearing state and the occurrence of a motion being not detected, select the first photodiode as the selected photodiode and measure the biosignal using a signal sensed by the first photodiode, and
in response to determining the wearing state of the electronic device to be the second wearing state and the occurrence of a motion being detected, select the second photodiode as the selected photodiode and measure the biosignal using a signal sensed by the second photodiode.

11. A method performed by an electronic device, the method comprising:
emitting, by a lighting-emitting diode (LED), light of a first polarization direction;
receiving, by a first photodiode, the emitted light through a first polarizer having the first polarization direction;
receiving, by a second photodiode, the emitted light through a second polarizer having a second polarization direction perpendicular to the first polarization direction;
receiving, by a third photodiode, the emitted light without a polarizer;
determining whether the electronic device is worn on a living object, based on luminous intensity of light sensed from each of the first photodiode and the second photodiode;
in response to determining that the electronic device is worn on the living object, determining, a wearing state of the electronic device representing a degree of tightness with which the electronic device is worn on the living object, to be one of a first wearing state indicating a first degree of tightness or a second wearing state indicating a second degree of tightness, based on the luminous intensity of the light sensed from the first photodiode and the luminous intensity of the light sensed from the second photodiode, wherein the first degree of tightness is greater than the second degree of tightness;
in response to determining the wearing state of the electronic device to be the second wearing state, monitoring whether a motion of the electronic device occurs based on a change in the luminous intensity of the light sensed from the second photodiode;
selecting a photodiode among from the first photodiode, the second photodiode, the third photodiode, based on at least one of the wearing state of the electronic device or occurrence of motion; and
measuring a biosignal using a signal sensed by the selected photodiode.

12. The method of claim 11, further comprising:
determining whether the electronic device is worn on the living object or the wearing state of the electronic device by receiving the luminous intensity of the light sensed from each of the first photodiode and the second photodiode at preset intervals.

13. The method of claim 11, wherein the determining whether the electronic device is worn on a living object comprises:
determining proximity between the electronic device and the living object based on a ratio of the luminous intensity of the light sensed from the first photodiode to luminous intensity of the emitted light.

14. The method of claim 11, wherein determining whether the electronic device is worn on a living object comprises:
determining that the electronic device is worn on the living object, in response to a signal indicating the luminous intensity of the light sensed from the second photodiode having a form of a pulse wave.

15. The method of claim 14, wherein the determining a wearing state of the electronic device comprises:
in response to determining that the electronic device is worn on the living object, determining the wearing state of the electronic device by comparing the luminous intensity of the light sensed from the first photodiode and the luminous intensity of the light sensed from the second photodiode.

16. The method of claim 14, wherein, based on a depth of the living object by which light having the first polarization direction emitted from the emitted light penetrates the living object of a user increasing, the luminous intensity of the light sensed by the second photodiode increases.

17. The method of claim 16, wherein, based on the luminous intensity of the light sensed from the first photodiode is higher than the luminous intensity of the emitted light, a distance between the electronic device and the living object is less than threshold distance.

18. The method of claim 16, wherein, based on the luminous intensity of the light sensed from the first photodiode is lower than the luminous intensity of the emitted light, a distance between the electronic device and the living object is more than threshold distance.

19. The method of claim 11, wherein the determining a wearing state of the electronic device comprises:
   in response to determining that the electronic device is worn on the living object, calculating a ratio of the luminous intensity of the light sensed from the first photodiode to the luminous intensity of the light sensed from the second photodiode;
   in response to the ratio being less than a threshold ratio, determining the wearing state of the electronic device to be the first wearing state; and
   in response to the ratio being greater than other threshold ratio greater than the threshold ratio, determining the wearing state of the electronic device to be the second wearing state.

20. The method of claim 11, wherein the measuring a biosignal using a signal sensed by the selected photodiode comprises:
   measuring the biosignal using only the signal sensed by the selected photodiode; and
   excluding, from measuring the biosignal, a signal sensed by the other photodiode different from the selected photodiode of the first photodiode, the second photodiode, and the third photodiode.

21. A non-transitory computer-readable storage medium storing instructions that, when executed by a processor, cause the processor to perform the method of claim 11.

* * * * *